US008382285B2

(12) United States Patent
Eberl et al.

(10) Patent No.: US 8,382,285 B2
(45) Date of Patent: Feb. 26, 2013

(54) DEVICE AND METHOD FOR DETERMINING THE ORIENTATION OF AN EYE

(75) Inventors: Roland Eberl, Muenchen-Neuried (DE); Matthias Mayer, legal representative, Munich (DE); Heinrich A. Eberl, Munich (DE); David Dickerson, Munich (DE)

(73) Assignee: metaio GmbH, Munich (DE)

( * ) Notice: Subject to any disclaimer, the term of this patent is extended or adjusted under 35 U.S.C. 154(b) by 0 days.

(21) Appl. No.: 13/300,691

(22) Filed: Nov. 21, 2011
(Under 37 CFR 1.47)

(65) Prior Publication Data
US 2012/0300978 A1    Nov. 29, 2012

Related U.S. Application Data

(62) Division of application No. 10/551,443, filed as application No. PCT/EP01/11634 on Oct. 8, 2001, now Pat. No. 8,113,657.

(30) Foreign Application Priority Data

| Oct. 7, 2000 | (WO) | PCT/EP00/09840 |
| Oct. 7, 2000 | (WO) | PCT/EP00/09841 |
| Oct. 7, 2000 | (WO) | PCT/EP00/09842 |
| Oct. 7, 2000 | (WO) | PCT/EP00/09843 |
| May 22, 2001 | (WO) | PCT/EP01/05886 |
| Jun. 8, 2001 | (DE) | 101 27 826 |

(51) Int. Cl.
*A61B 3/14* (2006.01)
(52) U.S. Cl. ........................ 351/210; 351/208
(58) Field of Classification Search .............. 351/200, 351/205, 206, 208, 209, 210, 221, 246
See application file for complete search history.

(56) References Cited

U.S. PATENT DOCUMENTS

| 5,163,002 A | 11/1992 | Kurami |
| 5,659,327 A | 8/1997 | Furness, III et al. |
| 5,815,741 A | 9/1998 | Okuyama et al. |
| 6,120,461 A | 9/2000 | Smyth |
| 6,227,667 B1 | 5/2001 | Halldorsson et al. |
| 6,636,185 B1 | 10/2003 | Spitzer et al. |
| 7,641,342 B2 | 1/2010 | Eberl et al. |
| 2007/0109619 A1 | 5/2007 | Eberl et al. |

FOREIGN PATENT DOCUMENTS

| DE | 4116255 A1 | 12/1991 |
| DE | 196 31 414 A1 | 2/1998 |
| DE | 197 28 890 A1 | 2/1999 |
| DE | 197 31 303 A | 2/1999 |
| WO | 93/18428 A2 | 9/1993 |
| WO | 99/42315 | 8/1999 |

(Continued)

OTHER PUBLICATIONS

Holographic Optical Elements (XP009022801), D.H. Close, Sep.-Oct. 1975, vol. 14, No. 5, Optical Engineering, pp. 408-419.

(Continued)

*Primary Examiner* — Jack Dinh
(74) *Attorney, Agent, or Firm* — Crowell & Moring LLP

(57) ABSTRACT

In a device or a method for determining the direction of vision of an eye, a starting point or a final point of a light beam reflected by a part of the eye and detected by a detector system, or of a light beam projected by a projection system onto or into the eye two-dimensionally, describes a pattern of a scanning movement in the eye. The inventive method uses a displacement device that guides the center of the pattern of movement into the pupil or macula center of the eye, and a determination device that uses the pattern of movement of the scanning movement to determine the pupil center or macula center.

15 Claims, 16 Drawing Sheets

FOREIGN PATENT DOCUMENTS

| | | |
|---|---|---|
| WO | 02/31578 A1 | 4/2002 |
| WO | 02/31579 A1 | 4/2002 |
| WO | 02/31580 A1 | 4/2002 |
| WO | 02/097511 A1 | 12/2002 |

OTHER PUBLICATIONS

International Preliminary Examination Report dated Jan. 1994 with an English Translation.

European Search Report dated Jan. 21, 2008.

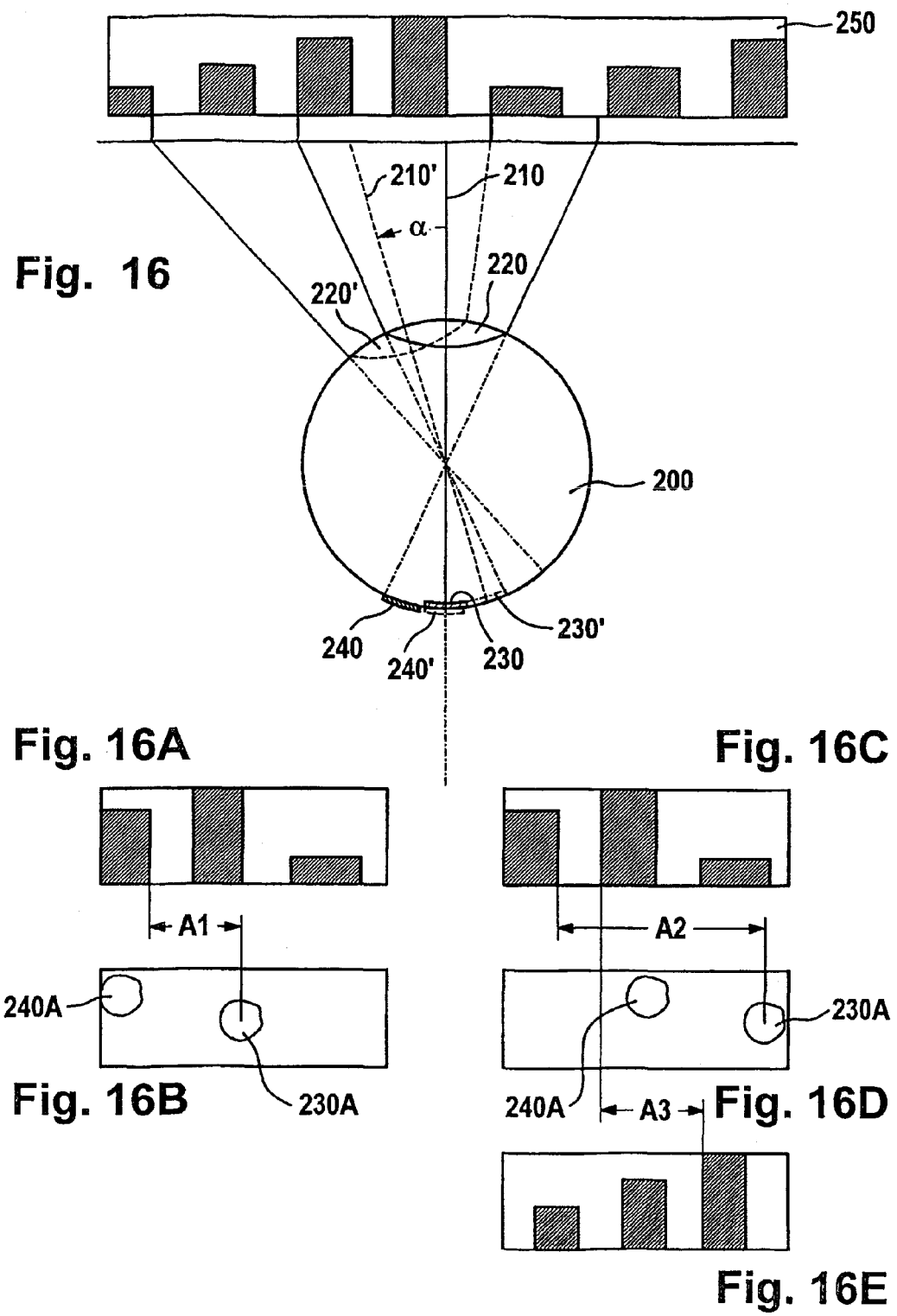

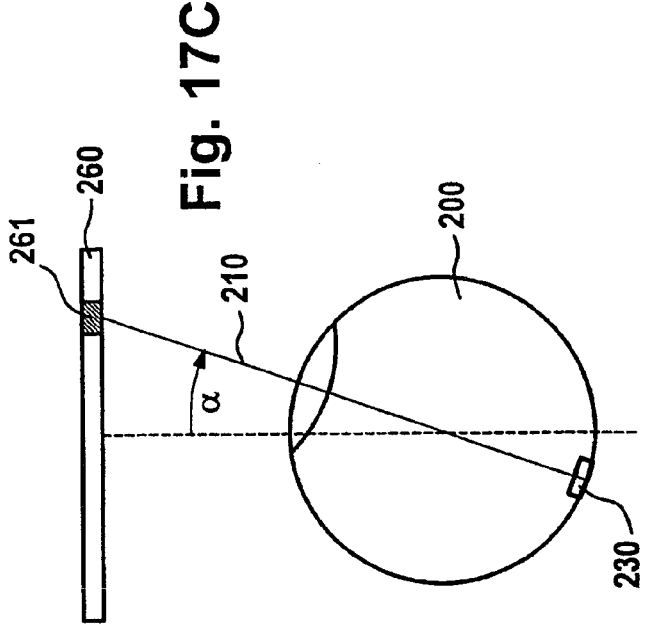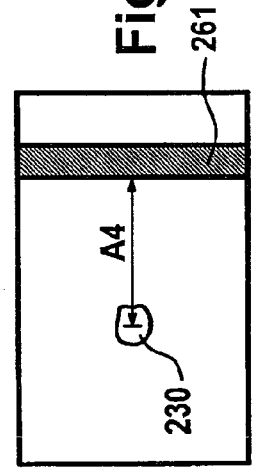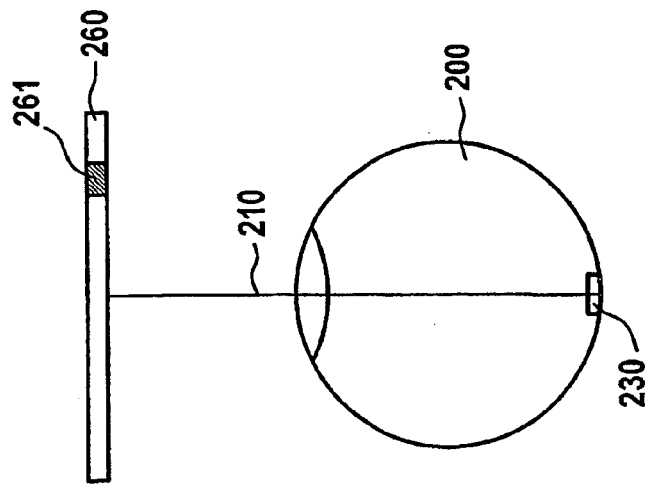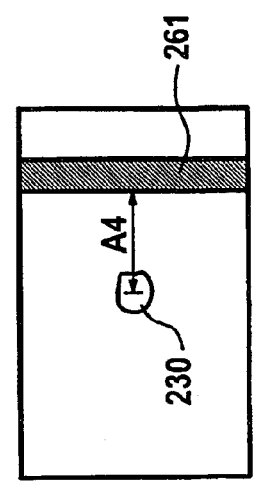

DEVICE AND METHOD FOR DETERMINING THE ORIENTATION OF AN EYE

This application is a divisional of U.S. patent application Ser. No. 10/551,443, titled DEVICE AND METHOD FOR DETERMINING THE ORIENTATION OF AN EYE, the entire disclosure of which is expressly incorporated herein by reference and which is the U.S. national phase of international PCT application PCT/EP01/11634, filed Oct. 8, 2001.

BACKGROUND OF THE INVENTION

1. Field of Invention

The present invention relates to a system and a method for determining the position and/or orientation, particularly the direction of vision, of an eye by the serial intercepting of a beam reflected by a part of the eye.

2. State of the Art

The knowledge of the momentary orientation of an eye is a necessary prerequisite for a plurality of the most different applications:

In medicine, the treatment of defective vision, retinal detachments, macula degeneration, etc. requires the detection of voluntary and mainly involuntary orientation changes of the eye in order to, for example, be able to appropriately cause a laser beam to follow in such a manner that, in each case, it impinges on the same point on the retina or moves along a certain trajectory on the retina.

In psychology, the orientation of the eye permits diverse conclusions. Thus, for example, a sudden strong rotation indicates the beginning of a grand mal or a black-out. Furthermore, significantly more extensive information can be obtained from the direction of vision of the eye, which can be determined, for example, by the mean perpendicular of the pupil. As an example, the recognition pattern of test persons when viewing certain pictures can be analyzed in this manner.

In addition, the knowledge of the direction of vision offers the possibility of using the information that indicates where the viewer is momentarily looking in order to identify the fixed object; whether it is a certain menu item on a (virtual) video screen, a device to be activated (light switch, etc.), a selected target of a rocket launcher, or the like.

Furthermore, the knowledge of the orientation and particularly of the direction of vision of the eye makes it possible to, for example, project visual information into the eye, which information is correlated with the viewer's perceived picture of the environment or his virtual orientation (for example, when using virtual-reality spectacles or the like), so that the pictures projected into the eye, for example, are seemingly resting in space or relative to an object, or the merged picture changes corresponding to the direction of the vision of the user of the virtual-reality spectacles.

Diverse devices and methods have therefore been developed for detecting the orientation of the eye:

German Patent Document DE 196 31 414 A1 mentions sensors which are fixed directly to the eyeball. These naturally, on the one hand, represent a considerable danger to and impairment of the test person, and, on the other hand, can also not detect the direction of vision of the eye (for example, in the case of strabismic persons) and, in addition, are quite inaccurate relative to the often minimal involuntary movements of the eye.

Furthermore, the integral taking of the retina reflex picture by CCD cameras is mentioned, which, on the one hand, because of the high exposure, is suitable for the low-light reflex picture but, on the other hand, comprises a very large quantity of data resulting in low processing speeds as well as distortion problems.

The above-mentioned document therefore suggests a device where an image of the environment reflected by the retina is serially scanned by means of a scanning device, is electronically modified and subsequently is projected back into the eye.

However, in this case, the orientation of the eye, particularly the direction of vision, is not determined but only a reflected and subsequently processed image of the environment is projected back into an eye on the same beam path in order to ensure a superimposing with the actually perceived image.

In the still unpublished Application PCT/EP01/05886, many different methods and devices are also described for the adaptation of an optical system to the direction of vision of the human eye.

It is therefore an object of the present invention to provide a device and a method by means of which the position and/or the orientation, particularly the direction of vision, of an eye can be determined rapidly and precisely.

SUMMARY OF THE INVENTION

This object is achieved by the characteristics claimed. Preferred embodiments of the invention are also claimed.

In the case of a device according to the invention or a method according to the invention for determining the position and/or the orientation, particularly the direction of vision, of an eye, a starting point or an end point of a light beam reflected by a part of the eye and detected by a detector system and/or of a light beam projected by a projection system onto or into the eye quasi two-dimensionally describes a movement pattern of a scanning and/or projection movement in the eye when the direction of the light beam is changed with respect to the time according to the scanning or projection movement.

A device according to the invention or a method according to the invention for determining the position and/or the orientation, particularly the direction of vision, of an eye according to the present invention is therefore based on the fact that that a light signal reflected by a part of the eye is detected by means of a detector system and is analyzed. In addition to the detector system, a device according to the invention may comprise additional optical devices, particularly a projection system.

The term "position" or "orientation" may apply to the position or orientation of the eye relative to the device (relative position) or relative to the environment (absolute position). In the following, for reasons of simplicity, position and/or orientation are sometimes combined in the term "orientation". The term "orientation" may therefore always apply to the kinematic orientation, to the kinematic position or to both.

As required, in the knowledge of the position or orientation of the device relative to the environment, which is determined, for example, by means of a suitable orientation determining device (laser triangulation, radar, Global Positioning System (GPS) receiver, and the like, both positions can be unambiguously converted to one another according to the rules of kinematics. In this case, the orientation determining device may be fastened to the device according to the invention itself (such as a GPS receiver with a pertaining analyzing unit), and/or can determine the orientation of the device according to the invention from the environment (for example, by means of laser triangulation, or the like). The determination of the orientation of an eye may also comprise the determination of a change of orientation of the eye with respect to a selected reference position.

In a preferred embodiment, the device according to the invention may be constructed in the form of spectacles. Likewise, it may, for example, also be arranged on or integrated in a frame wearable on the head, a helmet, or the like. In the same manner, it may, for example, also be arranged on or integrated in a stationary apparatus which uses the information concerning the orientation of the eye supplied by the device according to the invention, for example, in an apparatus for laser surgery or the like. Furthermore, it may be arranged on or integrated in an object which is movable relative to the environment and relative to the carrier, as, for example, a portable electronic notebook, a laptop or the like.

In the following, various characteristics are now suggested for each of the terms "part of the eye", "light signal", "optical device", "detection and analysis", which, in the case of a device according to the invention or a method according to the invention may be combined as an alternative or jointly.

It is pointed out expressis verbis that the present invention comprises all conceivable combinations of the described characteristics, unless the combination does not make any sense to the person skilled in the art from the start.

Wherever it is expedient, characteristics of a method according to the invention will be described in the following. In this case, a device is also always explicitly disclosed which is suitable for implementing the suggested method; for example, an appropriately programmed computer; sensors which are capable of supplying the necessary information signals; signal processing devices which are capable of appropriately processing these signals (filtering, digital-to-analog or analog-to-digital converting, storing, or the like) etc. Inversely, a corresponding method is also always disclosed by means of the function of the device according to the invention.

In the following, preferably the straight line through the pupillary center and the fovea centralis is defined as the direction of vision of an eye because, as a rule, a human being will direct his eye to a point to be viewed in such a manner that this point is imaged in the region of the sharpest vision. Bibliographically, a multitude of different axes of the eye is used, such as the fixation axis through the fixed viewed point and the fovea centralis, the visual axis through the nodal point and the fovea centralis or the achromatic axis—the axis with a disappearing transversal chromatic aberration—, which are each defined by geometrical relationships (straight lines through the fovea centralis, the pupillary center, the lens center, the focal point, etc.). The present invention is not limited to the above-mentioned definition of the direction of vision. As an alternative, any of the straight lines familiar to a person skilled in the art can be used as a direction of vision.

1. Light Signal 1.1 Definition

The essence of the invention is a light beam reflected by a part of the eye, which light beam is used for determining the orientation and particularly the direction of vision of the eye. In this case, a beam of rays is always called a light beam in accordance with geometrical optics. Its diameter may be very small; in borderline cases, infinitely small (the light beam will then change into the so-called principal ray), preferably less than or equal to the entrance pupil of the detector. In this case, it was surprisingly found that, contrary to a prejudice existing in the state of the art, also very small beam diameters can be used when sufficiently strong light sources (such as lasers or the like) and/or sufficiently sensitive detectors are applied. Furthermore, it is explicitly pointed out that the term "light beam" may comprise electromagnetic radiation of any wavelength, in addition to the visible, thus particularly also infrared light. The term "reflected" light beam comprises light beams generated in the eye, for example, the thermal radiation of blood vessels in the retina as well as light beams reflected or scattered on parts of the eye, which fall upon the eye from the outside.

1.2 Passive Scanning

Ambient light can preferably be used as reflected light, which ambient light which is incident in the opened eye from the environment and is reflected there on at least one part, such as the retina. Subsequently, in a pixel-type manner, one light beam respectively is selected and detected or intercepted from this reflected light in a targeted manner by a detector system. In the following, this is called "passive scanning".

Reflected light may also be light which is emitted by a part of the eye, for example, thermal radiation. Subsequently, in a pixel-type manner, one light beam respectively is selected and intercepted or detected from this emitted light by suitable devices. In the following, this is also called "passive scanning".

Advantageously, no projection system is required here. Neither is an interfering additional image signal projected into the eye. Furthermore, light beams of particularly suitable wavelengths can be filtered out of the polyspectral ambient light.

1.3 Active Scanning

As an alternative, according to the invention, light can first be actively projected into the eye by means of a projection system, such as a laser or another radiator, and a beam reflected at the corresponding part of the eye can subsequently be intercepted or detected. In the following, this is called "active scanning".

1.3.1 Modulation

According to the invention, the light actively beamed into the eye may be appropriately modulated, for example, in order to be able to easily differentiate it from the ambient light by means of a corresponding signal processing or to be able to determine the point in time of its emission. In this case, one or more characteristic quantities of the actively beamed-in light, such as the intensity, the wavelength or frequency, the polarization, the radiance or the like, are always changed over time.

1.3.1.1 Amplitude Modulation

In the following, amplitude modulation is a modulation in which at least one of the above-mentioned characteristic quantities each have defined values in different time segments or at different points in time. A light that is modulated in such a manner can be differentiable, for example, from ambient light on the basis of the characteristic quantity and/or the point in time of its emission can be determinable.

1.3.1.2 Frequency Modulation

As an alternative to or together with the above-described amplitude modulation, the actively beamed-in light signal may also be frequency-modulated. In the following, frequency modulation is the change of a periodicity of at least one of the above-mentioned characteristic quantities; i.e., one of the quantities changes periodically, and the period length of this periodic change has defined values in different time segments or at different point in time. By means of the period length of a reflected detected light signal, for example, the point in time of the emission of this light signal and thereby the propagation time of the light signal can be determined.

1.3.1.3 Other Modulations

One or more characteristic quantities of the actively beamed in light beam may also be simultaneously or successively amplitude- and/or frequency-modulated. Furthermore, analogously, not only the value (amplitude modulation) of at least one characteristic quantity of the light beam and/or the periodicity (frequency modulation) of this quantity can be modulated, thus, have respectively defined values in different time periods, but, for example, also the phase angle of periodically changing quantities (phase modulation).

The light signal may also be modulated in a different manner such that it contains information, for example, as to when it was emitted or information characterizing the light signal in contrast to ambient light.

1.3.2 Adaptation of the Active Luminous Intensity

In contrast to the passive scanning, the active scanning has the advantage that it can be ensured that light of sufficient intensity is always reflected from the eye in that a correspondingly large amount of light is actively beamed into the eye and reflected by it.

1.3.3 Beam Diameter
1.3.3.1 Point-Focal Illumination

According to the invention, a light beam, which may have a very small diameter, can be emitted by a radiator, such as a laser, and can be directed such that successively, i.e., sequentially, different points can be illuminated on the part of the eye (point-focal illumination).

The light beams reflected at these points can be detected in a targeted manner by a detector system (point-focal scanning). For example, a light beam is emitted in each case and the reflected light beam is detected in the detector system.

Likewise, in the case of a point-focal illumination, a detector system can also detect a larger area; i.e., it can simultaneously detect light beams which are reflected at difference points (areal scanning). Since, in each case, only one point is actively illuminated, the detector system in each case also only receives one actively beamed-in and reflected light beam. This is advantageous because the detector system does not have to be successively focused on different points or be adjusted to light beams of different points. It should be noted that a point-focal or areal scanning is also conceivable in the case of a passive scanning and/or areal illumination.

1.3.3.1.1 Detection of Light from the Entire Pupil

A light beam beamed into the eye, which preferably may have a very small diameter, at a reflecting part of the eye, for example, the retina, is for the most part reflected back or scattered back into a defined direction. A portion of these light beams reflected or scattered into another than the defined direction leaves the eye through the pupil and extends approximately coaxial with respect to the reflected principal ray. The reflected light beams which just barely still pass through the pupil are called marginal rays. The detector system is preferably constructed such that these marginal rays can also be detected, whereby the detectable light quantity is advantageously increased.

1.3.3.2 Areal Illumination

Instead of an individual light beam having a possibly very small diameter, a larger area of the eye can also be actively illuminated in a areal manner (areal illumination). For example, a light beam having a larger diameter can be directed onto the eye such that in each case an entire area of the retina or of the cornea is illuminated and reflects light. From this reflected light, a reflected light beam used for determining the orientation can then be analogously selected for the passive scanning by the detector system (point-focal scanning).

As in the above-described areal scanning, the detector system can also detect a larger area.

The actively beamed-in light can appropriately be modulated such that it can be selected particularly well in that it has, for example, a defined wavelength, polarization, etc. The illuminated area may comprise the entire part of the eye on which light is reflected and detected for the determination of the orientation. As an alternative, partial areas may also be illuminated successively so that in each case at least the point at which light is reflected and detected for determining the orientation of the eye is illuminated.

1.4 Mixed Operation

According to the invention, active scanning and passive scanning may be combined. For example, the light perceived by the eye is detected from the reflected ambient light and additionally a light beam is actively beamed in order to detect certain structures, marks or characteristics of the eye (fovea centralis, blind spot, etc.). The combination may advantageously be variable so that, for example, in phases of sufficient ambient light intensity, no active scanning takes place and, as soon as too little ambient light is reflected, additional light is actively beamed in.

Advantageously, different passive and/or active scanning methods can also be combined. Thus, the advantages of both methods can be combined. For example, actively beamed-in light that is reflected on the retina can be detected in the infrared range or infrared light emitted by the blood vessels of the retina can be detected; i.e., many light beams can be detected in order to, for example, precisely detect individual blood vessels for determining the orientation. Simultaneously, an image of the environment reflected by the retina can be detected in order to determine a correlation of the perceived image with the blood vessels. From the correlation between the blood vessels fixed with respect to the eye and an image fixed with respect to the environment, the orientation of the eye relative to the environment can then be determined.

1.5 Wavelength

In the case of the passive scanning, as described above, certain wavelengths can be filtered, i.e., absorbed or permitted to pass from the ambient light, which may comprise the range of the visible light as well as the remaining spectrum of electromagnetic radiation, particularly infrared radiation, which wavelengths can, for example, be detected particularly well. In the case of the active scanning, also visible light as well as electromagnetic radiation of other wavelength ranges, particularly light from the ultraviolet and infrared range, can be used. Infrared light is particularly advantageous because the additional active signal is not perceived by the eye.

1.6 "Flying Spot"

In the case of the passive as well as in the case of the active scanning, reflected light beams are preferably serially intercepted and analyzed; i.e., light beams which are reflected by certain points ("pixels") along a curve on the concerned part of the eye are successively detected by the detector system. This sequential scanning is called a "flying-spot" method because here the point of vision ("spot") of the detector system quasi moves along the curve. Generally, scanning and projection methods by which spatially bounded areas are typically serially scanned or illuminated along a straight or bent curve are frequently called "flying-spot" methods in technical terminology.

In the present application, mathematically any arbitrary continuous or discrete sequence of two-dimensional or three-dimensional points is called a curve, in which case, one or more values may be assigned to each point. In order to avoid confusion, the curve of the points of the eye which are illuminated or scanned will in the following be called a trajectory or pattern of movement. This means that the starting or end points of the illuminated or detected light beams describe a two- or three-dimensional pattern of movement in the or on the eye. The pattern of movement which is the result of the scanning or detection of the light beams is called the pattern of movement of the scanning movement or scanning pattern. The pattern of movement which is obtained during the projection of the light beams is called the pattern of movement of the projection movement or the projection pattern.

In the case of the areal scanning, a three-dimensional, as a rule, curved structure of the eye is imaged on a two dimensional picture. Undesirable distortions occur in this case. Furthermore, the focusing onto a three-dimensional surface is problematic.

In the case of many conventional eye-related information systems, optical signals are detected by means of a flat detector flatly from the eye or are projected by means of a flat projector flatly into the eye. This approach has the disadvantage that an optically correct imaging of a curved eye part on a flat detector or of a flat projector onto a curved eye part can be achieved only at considerable expenditures. This problems occurs to a considerably reduced extent in the case of the flying-spot method.

Advantageously, in the case of the sequential or point-focal scanning, one point respectively of a structure of the eye is imaged on a scanning element. As a result, the above-described distortion or focusing problems can be reduced.

The use of light beams of a small diameter is therefore also advantageous. The used light beams at the air/eyeball transition therefore advantageously have a diameter of less than 100 μm, preferably of less than 50 μm, particularly preferably of less than 10 μm, or particularly advantageously of less than 5 μm.

In addition, because of its compatibility with a holographic element, the flying-spot method is preferably used in the method according to the invention.

1.6.1 Spiral, Circular or Elliptical Scan

When mechanically controlled deflection devices are used, such as mirrors or the like, circles, ellipses or spirals are advantageously used as curves because, in this case, the deflection devices carry out harmonic movements (for example, a sinusoidal up-down movement or the like; see Section "Optical Devices"), which considerably reduces the excitation of undesirable oscillations of these devices. This ensures a higher precision of the determination of the orientation of the eye because of reduced systematic errors during the beam deflection. Likewise, for example, a lattice line pattern can be followed.

Even without mechanical deflection devices, for example, circles, ellipses or spirals are advantageously used as curves: The human monocular perception essentially is rotationally symmetrical about a visual axis extending through the fovea centralis and the optical center of the lens. Correspondingly, many parts of the eye, such as the iris, the pupil, the cornea, the lens and, in some aspects, also the retina in most people are constructed approximately rotationally symmetrically about the visual axis.

According to the invention, preferably according to the flying-spot method, the eye is therefore scanned by means of a spiral- or circle-shaped scanning or projection pattern, preferably about the visual axis, in which case, "circle-shaped" may mean a plurality of concentric circles. When the projection or scanning beams are disposed correspondingly diagonally with respect to the visual axis, the use of an elliptical scanning or projection pattern may be advantageous, as described in German Patent Document DE 197 28 890 A1. To this extent, reference is made to the full content of German Patent Document DE 197 28 890 A1.

1.6.2 Beams Perpendicular with Respect to the Eye

When light beams are perpendicularly incident on the air/eyeball transition, a certain fraction of the light is reflected back in the opposite direction to the incident light beam, while the remaining fraction penetrates quasi unhindered, after which it is absorbed or scattered by "lower-lying" fractions of the eye. The former analogously applies to light beams exiting from the eye by way of the cornea/air transition.

In the case of the method according to the invention, the projection or scanning preferably takes place according to the flying-spot method. In this case, a "narrow" light beam is preferably used which, at the air/eyeball transition, has a diameter that is insignificant in comparison to the curvature of the eyeball, particularly with respect to the curvature of the cornea. The light beam is preferably projected or scanned such that all its individual rays meet the air/eyeball transition in a manner as perpendicular as possible.

The cornea, i.e., the air/cornea transition, causes approximately 80% of the refraction exercised by the eye upon an incident light beam. Thus, the above-described approach not only has the advantage that little light is refracted at the air/cornea transition into a useless direction, but also has the advantage that the beams experience a slight refraction by the optical system of the eye. This has a positive effect not only on the spatial projecting or scanning precision but is also advantageous for applications in which the geometry of the light beams plays a significant role.

The fact that beams incident perpendicular to the eye are partially reflected back in the opposite direction can be used for obtaining information concerning the topology of the eye. This can take place, for example, by way of a projector—detector arrangement comprising a projection system and a detector system, which arrangement projects light approximately perpendicularly onto the eye and subsequently determines the coaxiality of the detected reflected-back light beam and of the projected light beam. When these light beams are not essentially coaxial (particularly the surface of the cornea has many microscopic and macroscopic irregularities and should therefore not be considered as a smoothly reflecting surface), the conclusion can be drawn that the projected light beam was not perpendicularly incident on the eye. Such information concerning the topology of the eye can be used for, among other things, the determination of the position and/or orientation of the eye.

A confocal arrangement of the projection system and of the detector system, for example, by way of splitter mirrors, is useful for such a projector—detector arrangement.

The use of a holographic element is advantageous particularly for the projection or the scanning of a light beam extending perpendicular with respect to the eye, because such a simple virtual development of a light guiding device makes it possible that light beams can be directed from a single projection system perpendicularly onto various regions of the eye and/or light beams perpendicularly exiting or reflected-back from various regions of the eye can be directed into a single detector system.

The various light signals which can be used for a device according to the invention as well as for a method according to the invention were described above. Next, the part of the eye will be discussed from which these light beams can be reflected.

2. Reflecting Part of the Eye

For determining the orientation and particularly the direction of vision of the eye, a light beam is detected which is reflected on at least one part of the eye. As a result of their reflection or emission behavior and particularly because of certain characteristic features existing on them, various areas of the eye can be used which will be discussed in detail in the following. However, light for determining the orientation of the eye can also be used that is reflected by other parts of the eye not explicitly mentioned here.

2.1 Cornea

According to the invention, light beams can be used for determining the orientation of the eye which are reflected by the cornea. Preferably those light beams are used in this case that are reflected on the exterior surface which is in the front in the direction of vision.

On its exterior surface, the cornea always has a plurality of microscopic (for example, small scars caused by foreign particles, such as dust, etc.) and/or macroscopic (for example, as a result of a surgical intervention on the cornea) irregularities which, although they have partially disappeared after a few days because of healing processes, for a sufficient time period, each represent a characteristic mark which is fixed to the body and can be optically detected with respect to the orientation of the eye. Likewise, the cornea may also have other significant characteristics, such as cloudiness or discolorations, which can also be used for determining the orientation.

For example, for determining the orientation of the eye, one or more of these irregularities can be detected and this irregularity or irregularities can be "followed" over time; i.e., for example, their respective position can be detected in a two-dimensional image. A change of the orientation of the eye can then be determined from the change of position of the irregularity or irregularities.

Likewise, for example, for determining the orientation of the eye, a reference map of the cornea can be established on which the position of different significant characteristics is stored with respect to a reference system of coordinates. When the eye is now scanned again in the same manner, an image or pattern identification can recognize the significant characteristics in the newly established map and, by comparing the position and orientation of the characteristics on the reference map or new map, can determine a change of the orientation of the eye (see also the "Analysis" section).

As an alternative or in addition, a light beam emitted or reflected by or at the surface of the cornea which is in the rear in the direction of vision can also be detected. By means of this light beam, for example, the characteristically dark reflex image of the macula fovea on the rear surface can be detected whose position on the cornea points directly to the orientation of the eye. Likewise, the phase shift between the light beams reflected on the frontal and on the rear surface can be determined (for example, according to Purkinje).

2.2 Sclera, Iris, Pupil

According to the invention, light beams can be used which are reflected by the iris or the adjoining sclera. Because of the considerably different degrees of reflection of the white sclera, the colored iris and the quasi light-swallowing pupil, as a rule, the transitions sclera/iris and/or iris pupil can be determined very easily and accurately from the reflected beams. As a result, for example, the position of the pupil and/or of the iris can be determined in that, by means of a considerably changing brightness of the reflected light a conclusion can be drawn with respect to the iris/pupil transition and thus points can be found on the circumference of the pupil (see "Analysis" section).

In addition or as an alternative, the structure of the iris can also be determined. The latter has characteristic features (patterns, color differences, injuries or the like) whose position can, for example, be stored in a reference map and can be compared with the actually identified position of the same features in order to determine an orientation of the eye. As in the case of the cornea, an orientation of the eye can therefore be determined by means of the detection of certain characteristic features.

2.3 Retina

According to the invention, light beams can preferably be used which are reflected by the retina. Characteristic features of the retina can be determined therefrom, such as individual larger blood vessels or the macula with the fovea centralis, which permit not only the determination of the orientation but, for example, together with the pupillary center, particularly also the direction of vision of the eye, which can be defined as a straight line through the pupillary center and the fovea centralis (see also the "Analysis" section).

Likewise, it is possible to detect an environment reflex image from the ambient light reflected by the retina, which allows conclusions on the perceived environment. For example, the orientation change of the eye relative to the environment can then be determined from a time-related displacement or distortion of the environment reflex image.

For the purpose of differentiation, in the following, the image of the environment, which is generated by light incident on the retina from the environment and at least partially reflected by the retina, is called an environment reflex image (of the retina) (passive scanning, while the image which is the result of light actively beamed into the retina and reflected by the latter is called a retina reflex image (active scanning). In addition, the term "retina reflex image", for the purpose of a more compact representation of the different variants, also comprises an image emitted by a part of the eye itself, such as the image of the heat radiation which the retina emits although this actually is not reflected light.

After the explanation of the different light signals and of different parts of the eye from which these can be reflected and used for determining the orientation of the eye, optical devices will be discussed in the following by means of which the light beams can be intercepted and, as required, reflected beforehand.

3. Optical Devices

The present invention comprises a detector system. It comprises a detector for detecting light beams which, as described above, are reflected by a certain part of the eye. In addition, the detector system may comprise a first light guiding arrangement (detector light guiding arrangement), for the deflection and/or focusing of light beams by means of which, for example, successively different light beams reflected by a part of the eye can be guided into the detector and/or can be focused on its receiver area. This guiding device is preferably designed such that light beams, which were reflected from different points of the eye, are successively, i.e., sequentially guided into the detector, so that the latter detects a corresponding sequence of scanning elements.

For the purpose of an active scanning, a device according to the invention, in addition to the detector system, may comprise at least one additional optical device, specifically a projection system for projecting light. The projection system comprises a radiator for the emission of light. Furthermore, the projection system may comprise a light modulation device in order to, for example, appropriately modulate the light emitted by the radiator. In addition, the projection system may comprise a projection light guiding arrangement, for example, for the deflection and/or focusing of the emitted light beams, by means of which, for example, successively, light beams, which are emitted by the radiator, are guided and/or focused onto certain points of the eye. Preferably, the detector light guiding device is at least partially used by the projection system. For example, light can first be actively beamed onto the eye and, on the same beam path, the reflected light can be guided into the detector. As a result, at least partially the same beam path is used for the projection and the detection. This is advantageous because, since systematic defects of the light guiding device can be compensated, the projection system can at least partially do without its own light guiding arrangement. Furthermore, it is advantageous that the detector quasi automatically detects the light signal emitted by the radiator and does not especially have to be adjusted to the reflecting point of the eye.

In the following, these individual elements of optical devices according to the invention will be explained in detail.

3.1 Detector

A detector system according to the invention comprises a detector for detecting light beams. The detector has a receiver area and detects at least one characteristic quantity of light beams which impinge on this receiver area, such as the radiation energy or the radiated power, the irradiance, the wavelength or frequency, the polarization or the like. The detector emits a signal corresponding to the detected quantity or quantities. By means of a suitable device, such as an analog-to-digital converter and/or a filter, as necessary, this signal can be appropriately processed before the emission. For example, an opto-electronic detector can detect an optical signal and emit a corresponding electrical signal; an opto-optical detector can detect an optical signal and emit a corresponding optical signal.

The detector may, for example, comprise a photodiode, in which current flows during the irradiation, from whose intensity the illuminance can be determined. The detector may also have a photo resistor whose ohmic resistance changes as a function of the absorbed light. From the change of the resistance, in turn, the irradiation can be determined. The detector may also comprise a photocell, a phototransistor, a photomultiplier, an image intensifier tube or basically any other component part that permits the detection of a physical quantity of a light beam impinging on the component part.

3.2 Detector Light-Guiding Arrangement

The above-described detector preferably sequentially detects light beams which are reflected by different points of the eye. For this purpose, the detector itself may be correspondingly constructed or controlled such that it can sequentially detect light beams in a targeted manner which impinge from different directions or on different points of its receiver area. As an alternative or in addition, a detector light-guiding arrangement may be present which in each case guides a light beam into the receiver area of the detector and/or focuses the light beam onto the receiver area. The detector light-guiding arrangement can be controlled such that light beams are sequentially guided onto the detector which impinge on the detector light-guiding arrangement from different directions. By means of a corresponding time-related controlling of the detector light-guiding arrangement, the light beams can be directed in a targeted manner sequentially onto the detector which were reflected by certain points of the eye. The spot of the detector thereby describes a pattern of movement on a part of the eye; it therefore scans this area by means of a certain pattern of movement.

Any device can be used as the detector light-guiding arrangement that fulfills this function; thus, can be controlled such that light beams are sequentially guided and/or focused from different, defined or definable direction in each case onto the receiver area of the detector. In the following, several conceivable characteristics of such devices will be explained in detail.

3.2.1 Mirrors

A detector light-guiding arrangement according to the invention may comprise one or more mirrors. Their orientation to one another, to the eye, whose orientation is to be determined, and to the detector can be adjustable such that light beams reflected by certain points of the eye are guided to the detector. Some of these mirrors may be arranged in a fixed manner with respect to the detector ("fixed mirrors"), while other mirrors may be adjustable in their orientation ("movable mirrors").

The orientation of the movable mirrors can be controllable such that a desired pattern of movement can be scanned; i.e., that light beams which were reflected by certain points of the eye are sequentially guided onto the detector. Because of the reversibility of the beam path, the detector light-guiding device can also be understood as if an imagined light beam were emitted by the detector and were guided and/or focused by the detector light-guiding arrangement onto the point of the eye which specifically is to be scanned by the detector.

3.2.2 Holography

Instead of the above-described mirrors, holographic elements can also be used which cause the desired deflection of the light beams. Compared with conventional mirrors, such holographic elements have several advantages. On the one hand, they have a lower weight than a mirror. On the other hand, they can be further developed such that they are not perceived by the eye itself. It is mainly possible to produce holographic elements having almost any reflection behavior. For example, a holographic element may reflect light only in a certain wavelength range. When this wavelength range is, for example, in the infrared range, the holographic element cannot be perceived by the eye.

A holographic element may, for example, be a holographic coating on a carrier.

When, instead of a movable mirror, a holographic element is used for the changeable deflection of light beams, the change of the orientation of the reflection required in this case can take place analogous to the movable mirror by an orientation change of the holographic element. However, the reflection behavior of the holographic element can, for example, also be changed electronically, which permits a considerably faster and more precise scanning. For this purpose, the holographic element has to be electro-holographic.

3.2.3 Other Elements

The detector light-guiding device may comprise other optical elements, particularly, for example, apertures, which limit the diameter of the detected light beam and thereby spatially limit the scanned area of the scanned part of the eye, or optical or electro-optical lenses which appropriately expand or focus the light beam, for example, on the receiver area of the detector.

3.3 Projection System

In addition to the detector and possibly the detector light-guiding arrangement, a projection system may be present for an active scanning, which projection system has a radiator that emits light beams. Further, the projection system may comprise a light modulation device for appropriately modulating the light emitted by the radiator. In addition, the radiator may comprise a projection light-guiding arrangement, for example, for the deflection and/or focusing of the emitted light beams, by means of which light beams emitted by the radiator are, for example, sequentially guided to and/or focused on certain points of the eye. These elements will be explained in the following.

3.3.1 Radiator

A radiator emits light beams which preferably impinge on a part of the eye and are reflected by the latter. In principle, any device that can emit light beams is therefore conceivable as a radiator, such as electric bulbs, lasers, LEDs or the like.

Advantageously, at least one of the physical quantities emitted by the radiator is adjustable, so that the emitted light can be differentiated from the ambient light. For example, a laser may only emit light in a certain narrowly restricted wavelength range, or the radiator emits light beams having a certain time-related pattern with respect to intensity, wavelength or the like.

In the case of the present invention, the term "radiator" may also comprise several individual light sources, such as varicolored LEDs or lasers which can emit light of different wavelengths.

3.3.2 Light Modulation Device

The light emitted by the radiator can be appropriately modulated in a light modulation device before it impinges on the eye. For example, a light modulation device may comprise a color filter which allows only light of a certain wavelength to pass. Likewise, a light modulation device may comprise a polarization filter which allows only light of a certain polarization to pass. Such and other filters may be controllable in such a manner that the light can be modulated over the time.

3.3.3 Projection Light-Guiding Arrangement

In order to guide light emitted by the radiator to from where it is to be reflected in order to subsequently be detected by the device according to the invention, a projection light-guiding arrangement may be present into which light enters that was emitted by the radiator and which guides this light to the desired area.

In principle, because of the reversibility of the beam path, an arrangement can be used for this purpose that is analogous to any of the described detector light-guiding arrangements.

In particular, the detector light-guiding device itself may form a part of the projection light-guiding arrangement in that the light emitted by the radiator enters in the opposite direction parallel into the beam path of the light detected by the detector system in front of, in or behind the detector light-guiding device. Such an arrangement has the advantage that possibly existing systematic defects are identical during the projection and scanning and compensate one another. Another advantage consists of the fact that the detector system quasi automatically detects the light beam which the radiator has emitted.

For this purpose, a splitter mirror may, for example, be present between the detector light-guiding device and the detector, which partially allows light coming from a radiator to pass into the detector light-guiding device, and partially reflects light coming from detector light-guiding device to the detector, in which case beams in the direction of the detector are preferably given priority. For example, the ratio of the beams reflected to the detector to the beams incident on the splitter mirror may amount to 95%, 90%, 85% or 80%. The ratio of the beams passing through the splitter mirror to the beams incident on the splitter mirror may, for example, amount to 5%, 10%, 15% or 20%. This means that a light beam impinging on the splitter mirror is reflected, for example, by 95% and can pass through the mirror by 5%.

The fact that such a splitter mirror hinders the projection beam is uncritical because this can be compensated by an increase of the radiator power.

3.4 Exterior Picture

In addition, a device according to the invention may comprise a device for taking a picture of the environment, such as a camera. This picture can be processed in order to, for example, identify significant patterns of the environment.

A picture of the environment taken by such a device can be compared in a suitable manner, for example, with an image of the environment ("environment reflex image") reflected at the retina or the cornea of the eye. For example, in both images, the same object can be identified and, from the spatial assignment of the two images of the object, the orientation of the device or of the eye relative to the environment can be determined.

Such a device for taking a picture of the environment can preferably be arranged approximately confocal with respect to the eye.

3.5 Position of the Device

In addition, a device according to the invention may comprise an orientation determining device for determining the orientation of the device in order to determine, for example, by means of an orientation of the eye relative to the device, an orientation of the eye relative to the environment.

Such an orientation determining device may be fixedly connected with the device according to the invention and determine the orientation and/or position of the device relative to the environment. An orientation determining device may, for example, comprise a GPS receiver and the pertaining analysis device which determines the position of the device from the received GPS signals.

Likewise, an orientation determining device may also be fixedly connected with the environment and determine the orientation of the device, for example, by means of triangulation or the like.

3.6 Markers

A device according to the invention may contain one or more markers. A marker may, for example, be arranged in front of the eye, either inside or outside the field of vision. Such a marker may, for example, be arranged on a spectacle lens in front of the eye.

A marker may, for example, be used for determining optical reference values. For example, a light beam reflected on such a marker may be detected by the detector. A characteristic quantity of this light beam can then be determined as a reference value, for example, for a 100% reflection.

Such a marker may also be used as a fixed point during the determination of the orientation of the eye with respect to the device. For example, such a marker may be present in such a manner that, in the addition to light beams reflected by a significant region of the eye (for example, the fovea centralis or the iris), the detector can also detect light beams which are emitted by the marker, for example, reflected. By means of the directions from which the respective light beams are detected, a position of the significant region of the eye relative to the marker and thus an orientation of the eye relative to the device can be determined.

Such a marker may also be used for calibrating or recalibrating the optical device. As a result of outside influences (such as a shock) or inside influences (such as a temperature (caused?) elongation), in the course of the operation, the position and orientation of individual elements of the optical device may change. For example, because of a deformation of the device on which they are arranged, the mirrors may change their position with respect to one another. In order to determine such a change, for example, a reference position of the marker can be determined first in that it is determined how the detector light-guiding arrangement has to be controlled so that the detector will detect light that is reflected by the marker. When then later, the position of the marker is determined analogously, the change of the optical device with respect to the marker can be determined from a change with respect to the reference position. When the marker is fixed with respect to the detector, the (apparent) change of position is based on a change of the detector light-guiding arrangement which can thereby be determined.

During the active scanning, a light beam can advantageously be beamed at the marker in a targeted manner and the reflected light beam can be detected by the detector, for example, in order to make one of the above-mentioned determinations (reference value, fixed point, calibration).

The marker may advantageously be further developed so that it cannot be perceived by the eye. The marker may, for example, only be visible in the infrared range, so that it can be detected by an infrared detector but is not perceived as being disturbing by the human eye. This can be implemented, for example, by means of a hologram.

As an alternative or in addition, a marker itself may also actively emit light.

Additional markers according to the invention or their use are disclosed in Section 4.3.

3.7 Focusing

The above-described optical devices, thus particularly the detector system and/or the projection system may comprise at least one suitable focusing device by means of which, for example, the distance of the scanned area from the detector and/or radiator can be adjusted, and it can thereby, for example, be determined whether the retina or the cornea is scanned or illuminated. In the case of light beams having small diameters, the benefit of such a focusing device may be limited.

After the listing and detailed explanation of the characteristics of the optical device which detect a light beam reflected by a part of an eye or beam light onto the eye, the detection of the light beams and the analysis of the thus obtained signals will be discussed in the following.

4. Detection and Analysis

It is an object of the present invention to determine the position and/or orientation, particularly the direction of vision, of an eye. In the following, it will be described how characteristics of the eye can be determined from light beams reflected by a part of the eye and subsequently detected by the detector system, and how these characteristics can be used for determining the orientation of the eye.

4.1 Detected Image

During the determination according to the invention, points are preferably scanned sequentially, i.e., after one another, along a trajectory. This means that light beams which are reflected by these points are sequentially detected in the detector system and at least one physical quantity of these light beams is determined, such as their intensity or brightness, radiation output, wavelength, gray-scale values or the like. The result is, for example, a sequence of scanning elements (i.e., a scanning element curve) to which, for example, values of the physical quantity or quantities and, for example, coordinates determined by means of the position of the detector light-guiding arrangement can be assigned (for example, abscissa x and ordinate y; radius R and polar angle $\phi$). The values of the physical quantity or quantities are also called an information content of the light (signal).

In the case of a finer scanning, i.e., for example, in the case of smaller steps between the individual positions (x,y) of the detector light-guiding arrangement, an increasingly sharper two-dimensional "picture" of the part of the eye can be determined from the picture element curve, by which the light beams are reflected. By means of the scanning according to the invention, a two-dimensional picture of at least one three-dimensional region of the eye can therefore be established, for example, of the cornea, the retina or the like.

If one of these regions is curved, it appears distorted in the two dimensional image. The orientation of the eye can be determined from such distortions. Depending on the orientation of the eye with respect to the detector, for example, a circular pupil may appear as an ellipse from whose principal axes the orientation of the eye can be determined.

Elements situated behind one another in the direction of view of the detector or of the detector light-guiding arrangement, i.e., against the direction of the light beams which are detected by the detector, mutually overlap in the two-dimensional image or have a certain distance. On the basis of such overlaps or distances, the orientation of the eye can in turn be determined. When, for example, the three-dimensional position of the pupillary center with respect to the fovea centralis is known, for example, empirically from statistical examinations or preceding determinations according to the invention, from the spacing of the images of the pupillary center and of the fovea centralis in the two dimensional image, their spatial position and thereby the orientation and/or position of the eye can be determined.

Likewise, the three-dimensional position of a detected point can be determined, for example, from the two-dimensional position of its picture element and the propagating time of the signal reflected on it, in which case the propagating time can be determined, for example, in the case of a frequency-modulated light signal by means of the frequency of the detected light signal. From the propagating time, for example, a distance of the detected point from the detector and thus the position of this point relative to the device can be determined. Likewise, instead of the propagating time, the focusing, i.e., for example, the adjusting of a focusing device can be used, which also supplies information concerning the distance of the detected point from the detector.

When, for example, by means of the propagation time, the distance of the reflecting point from the detector is determined, a z-value can additionally be assigned to each picture element, so that the three-dimensional position of the scanned points relative to the device according to the invention can be determined. In this case, a quasi three-dimensional image of the eye can be scanned. For reasons of simplicity, in the following, reference is mostly made to two-dimensional images. However, by means of the above-illustrated three-dimensional picture elements, an analogous three-dimensional method may also always be used. When, for example, a position of the picture element in the two-dimensional image is mentioned, by means of an additional measuring of the distance of the point, which reflects light, with respect to the detector, the three-dimensional position of the point relative to the device or relative to other points can also be determined.

The two-dimensional images of the same three-dimensional structure of the eye, which is scanned in various orientations, are not only shifted or rotated with respect to one another (from which, in reverse, the orientation change of the eye can be determined) but are also distorted differently. At a preferred high scanning frequency in comparison with the speed of the eye movement, however, the distortions differ only slightly in the case of images which are rapidly scanned sequentially, so that they can be roughly neglected and the two-dimensional images can be used directly without taking into account the different distortions. When the orientation of the eye changes noticeably, the distortions in the various two-dimensional images may also clearly differ from one another so that such images can, for example, no longer be compared with one another in a suitable manner. It may therefore be advantageous to again scan certain images at certain time intervals or in the event that a clear orientation change is detected.

4.2 Strategy

By means of the detected picture elements, the position of certain characteristic features or structures of the part of the eye, which reflects the detected light, can be determined within the image.

For this purpose, the eye can be scanned along a suitable trajectory. This trajectory may, for example, be selected such that particularly significant characteristics, for example, changes of the reflectivity or the like, are detected with high probability.

For example, the position of the pupillary center and/or of the macula center can be determined. This may be relevant for determining the direction of vision.

Several of the described methods can also be carried out successively, in which case the information obtained in a preceding method can be used for subsequent methods. As an example, the pupillary center can first be roughly determined. The thus found approximate center is stored and is used as a starting or reference value for the precision determination of the actual pupillary center. The approximate or the actual pupillary center can, in turn, serve as a starting value or preliminary macula center when determining the macula center because, with a certain probability, for example, the macula center may be situated in a certain position with respect to the pupillary center. This position may be known or estimated, for example, empirically from statistical investigations and/or preceding determinations according to the invention. For example, in the direction of vision of the eye, with a high probability, the macula center may be situated directly behind the pupillary center.

In particular, all methods described above and below can be "readjusted" by means of already identified characteristics; i.e., already identified characteristics can be used as reference and starting values for subsequent methods. For this purpose, a reference point, for example, can be determined, and then one or more optical devices, thus, for example, the detector light-guiding device and/or the projection light-guiding device can be aligned with respect to this reference point.

Advantageously the scanning can be carried out at a high scanning frequency. As a result, the orientation of the eye between two or more successively scanned images advantageously changes only little. As a result, the position of significant characteristics within the scanned images also changes little, which can advantageously facilitate the search for these characteristics.

4.3 Analysis

When, after at least one of the above-mentioned processes, the two- or three-dimensional position of one or more significant characteristics of the eye has been determined, orientations of the eye relative to the device and/or the environment can be determined therefrom in various manners. Here, it should be pointed out that orientation may also comprise the determination of a change of the orientation with respect to an orientation selected as a reference.

For the purpose of an explanation, for example, in a simple case, the orientation of an eye at a certain point in time may be selected as a reference, and the position of the pupillary center may be determined in an image of the light reflected by the sclera or the iris. When, at a later point in time, the position of the pupillary center is again determined in an image of the light reflected by the sclera or the iris, a corresponding rotation of the eye can be determined from the new position of the pupillary center relative to the old position. When, in addition or as an alternative to the position of the picture element, for example, the distance from the detector is determined, the position of the element and thus of the eye relative to the device according to the invention can also be determined therefrom.

In the following, several possibilities will be explained as examples for the determination of the orientation, particularly of the direction of vision.

4.3.1 Determination of the Visual Axis

A straight line through the center of rotation of the eye and the center of the pupil, for example, is assumed to be the direction of vision or the visual axis.

When the position of the pupillary center is determined for different positions of the eye, the images of the pupillary center in a two-dimensional scanned image are situated within a circle (or because of the distortion by the two-dimensional imaging of the three-dimensional eye, within an ellipse) around the imagined image of the center of rotation which can thereby be determined (for example, as a statistical center of the images of the pupillary center). In a simplified manner, the straight line through the center of rotation and the pupillary center then represents the visual axis of the eye according to the assumption. For the purpose of clarification, a pure rotation of the eye should, for example, be considered about a vertical axis through the center of rotation. The two-dimensional image of the pupillary center in this case moves on a horizontal straight line in an image plane perpendicular to the viewing direction and parallel to the vertical axis of rotation. In the case of very many taken picture elements, the main emphasis of this straight line corresponds approximately to the image of the center of rotation.

Likewise, for example, from the distortion of the pupil, which appears as an ellipse in the case of a non-frontal top view, the plane of the pupil can be determined by a principal axis transformation; the mid-perpendicular of the plane of the pupil can be assumed to be the visual axis.

Likewise, the visual axis can be determined as the connecting straight line of the fovea centralis and the pupillary center. The three-dimensional position of the pupillary center and the fovea centralis can be estimated, for example, by means of empirical data from the position of the pupillary center and the position of the fovea centralis relative thereto. For this purpose, stored values, for example, can be used for this position, which are known from earlier investigations (for example, the so-called Gullstrand values) or values which were determined by means of a device according to the invention. Likewise, as described above, the distance of the pupillary center and/or of the fovea centralis from the detector can be determined by means of the propagation time of the reflected light beam between the emission and the detection and/or by means of the focusing and, together with the two-dimensional position of the picture elements, the three-dimensional position of the pupillary center and/or of the fovea centralis can be determined therefrom.

4.3.2 Determination of the Orientation by Means of a Map

For determining the orientation of the eye, according to the invention, a reference map of a part of the eye can be established in which significant structures, such as the macula, blood vessels of the retina, injuries of the cornea or the like, can be recognized. These characteristics can advantageously be entered on a corresponding reference map by means of image or pattern identification.

A reference image and/or a reference map may be implemented, for example, by means of a memory, in each of the memory locations, the value of the characteristic quantity of a detected light beam assigned, for example, according to the position, being stored. Advantageously, the characteristic values may previously have been filtered such that memory locations are only occupied by a defined characteristic value, for example, a value higher than a defined threshold value. In a reference map, significant structures of the scanned reference image may already be imaged and stored with a low storage requirement.

When now, at a later point in time, according to the invention, a part of the eye is scanned on which the structures detected as described above are at least partially present—advantageously the same area as during the establishment of the reference image—points of an actual image detected in such a manner can be caused to be congruent with the reference image or the reference map by means of a corresponding routine. From the resulting rotations and displacements of the actual image, the change of orientation of the eye with respect to the point in time of the taking of the reference image can be determined. In this case, the actual image can be taken by means of a different trajectory than the reference image. In particular, it may clearly have fewer picture elements. Here, it is particularly advantageous that causing the congruency of a few actual picture elements with a few reference points can permit a fast and simple determination of the orientation. Likewise, by means of the actual image, an actual map can be established and be caused to match the reference map, the change of the orientation of the eye again being determinable from the occurring rotations and displacements.

Advantageously images can be scanned at a high scanning frequency, so that the orientation of the eye changes little between two or more successive scannings. This can advantageously simplify the comparison of an actual image with a reference image or a reference map because the position of the picture elements of the same point in or on the eye has changed little, and the correlation between the picture elements of different scanning points in time can be easy to establish.

As described above, it may be advantageous to again detect (scan?—transl.) a reference image or a reference map when it is found that the orientation of the eye has changed so much that, as a result of the distortion because of the two-dimensional imaging of a three-dimensional structure, matching becomes difficult or impossible. A correspondingly severe change of orientation of the eye can be determined, for example, in that it is no longer possible to cause an actual image and the reference image or the reference map to be congruent.

4.3.3 Orientation with Respect to the Environment and/or the Device

According to the invention, generally the absolute and/or relative position and/or orientation, particularly the direction of vision, of an eye relative to the environment and/or to the device according to the invention can be determined. This results in different possibilities of determining the orientation, of which some will be explained in detail in the following.

4.3.3.1 Relative Kinematics

A number of possibilities were explained above in the manner of examples with respect to determining the orientation of the eye relative to the device and particularly the direction of vision of the eye by means of one of more images which can be created by detecting light beams reflected by a part of the eye.

When, as indicated above, in addition, the position of the device relative to the environment is determined, for example, by means of magnetic, IR or RF position finding of the device from an inertially fixed device or by means of a GPS receiver on the device according to the invention, the orientation of the eye with respect to the environment can be kinematically calculated from the relative orientation of the eye with respect to the device and the relative position of the device with respect to the environment.

Inversely, when the orientation of the eye relative to the environment is known and the orientation of the device relative to the environment is known, the orientation of the eye with respect to the device is obtained analogously.

When, for example, the orientation of the eye with respect to the environment is described by means of the angles $\phi_{AU}$, $\eta_{AU}$, $\phi_{AU}$), the orientation of the device with respect to the environment is described by means of the angles ($\phi_{VU}$, $\eta_{VU}$, $\phi_{VU}$), and the orientation of the eye with respect to the device is described by the angles ($\phi_{AV}$, $\eta_{AV}$, $\phi_{AV}$), the orientations expressed by the respective imaging $A_{xy}$ from x to y can be changed into one another:

$$A_{AU} = A_{VU}(\phi_{VU}, \eta_{VU}, \phi_{VU}) * A_{AV}(\phi_{AV}, \eta_{AV}, \phi_{AV})$$

$$A_{AV} = A_{VU}(\phi_{VU}, \eta_{VU}, \phi_{VU}) * A_{AU}(\phi_{AU}, \eta_{AU}, \phi_{AU})$$

The second equation therefore indicates, for example, that the imaging of a coordinate system fixed to the eye onto a coordinate system fixed to the device and thereby the orientation of the eye relative to the device can be determined from a suitable linking of the imaging from the coordinate system fixed to the eye onto a coordinate system fixed to the environment and an imaging of this coordinate system fixed to the environment onto the coordinate system fixed to the device. These two imagings can be determined by the orientation of the eye relative to the environment and of the device relative to the environment.

In the following, images are compared with one another which are fixed with respect to the environment (environment image), with respect to a device according to the invention (device image) or with respect to the eye (eye image). These images are preferably compared with one another in a common coordinate system, for example, a coordinate system fixed with respect to the device; i.e., for example, at least two images respectively are illustrated in this coordinate system and significant structures in the images are assigned to one another. This means, for example, that their relative position and/or orientation with respect to one another is determined. Analogous to the "orientation" of an eye, the "position" of characteristics, structures, etc. comprises the position in a narrower sense, characterized, for example, by distances from coordinate axes, and/or their orientation in a narrower sense as in the remaining application, characterized, for example, by angles with respect to coordinate axes.

By means of the change of these relative positions, the change of the pertaining images with respect to one another can be determined in each case. From this change, the corresponding orientation change of the pertaining systems (eye, device, environment) with respect to one another can in each case be determined. For example, from a displacement of an eye image with respect to a device image, a corresponding distortion of the eye with respect to the device can be determined.

As an alternative or in addition, an absolute assignment of the pertaining systems can also be determined from the relative positions. For example, from the relative position of a significant structure in an eye image (for example, of the macula) with respect to a significant structure in an environment image (for example, an edge, a tree or the like), the position of the eye with respect to the environment can be determined. Thus, it can, for example, be determined where the eye is looking relative to the significant structure in the environment (for example, directly at the edge, at the tree or the like).

In the following, some of these possible determinations will be explained in detail.

4.3.3.2 Eye—Environment

When an image fixed relative to the environment (environment image), such as an image of the environment which is taken by a camera fixedly connected with the device, is compared with an image fixed relative to the eye (eye image), such as an image of the retina or of the cornea which is, for example, a result of an active scanning, an orientation of the eye relative to the environment can be determined therefrom. When images taken at different times are compared, a change of orientation of the eye relative to the environment can be determined therefrom.

4.3.3.2.1 Relative Orientation Eye—Environment

For determining the orientation of the eye relative to the environment, an environment image and an eye image are viewed in a common coordinate system, for example, in a coordinate system fixed with respect to the device (device-fixed coordinate system).

In this case, the images can be appropriately imaged in this coordinate system. For example, from the known geometry of the arrangement of a camera, which supplies the environment image, with respect to the device, which supplies the eye image, it can be determined how the environment image is to be transformed into a device-fixed coordinate system of the eye image. Likewise, for example, a significant shape of the device, for example, the geometrical shape of a pair of spectacles, may be recognizable in the environment image. By means of the significant shape of the device in the environment image, it can then be determined how the environment image is to be transformed into the device-fixed coordinate system of the eye image.

Advantageously, an image of the environment reflected by a part of the eye can be used as the environment image, such as the environment reflex image of the retina or the cornea because the environment image and the eye image are then already present in the same device-fixed coordinate system.

These images are compared with one another; i.e., certain significant structures within the environment image (edges, objects, letters, etc.), which can be identified, for example, by means of pattern identification, are assigned to certain significant structures of the eye image (for example, the macula, the pupillary center, etc.), and their position relative to one another is determined.

By means of this relative position, the orientation, particularly the direction of vision, of the eye relative to the environment can be determined.

For example, it can be determined in the eye image at which point the macula center is situated. This point can be determined in the environment image. It can then be determined that the viewer's eye is looking specifically at this point in the environment. As a result, the direction of vision of the eye relative to the environment can be determined. Advantageously, a pattern identification can identify the object in the environment image at which the viewer is just looking, for example, which switch, which target or which object.

Advantageously, an environment image which is taken by means of a camera (camera picture) can be correlated with an environment image which is reflected by the eye and scanned (environment reflex image). The two images can be assigned to one another such that a point of the environment which is defined in one image can be determined in the other image. For example, in a relatively blurred and/or low-light environment reflex image, by means of the method according to the invention, the point of the environment can then be determined at which the eye is looking, and this point or the pertaining object, switch, etc., can be better identified in a more focused and/or more luminous camera picture by means of pattern identification. This is, for example, advantageous in the case of diffuse light at which an infrared camera can scan a more precise image of the environment.

4.3.3.2.2 Relative Orientation Change Eye—Environment

Likewise, a change of the orientation of the eye relative to the environment can be determined in that, analogous to a method according to the invention, at different points in time, in each case, one orientation of the eye with respect to the environment is determined, and the change between the orientations determined at the different points in time is indicated.

For example, significant characteristics in the environment image (edges, etc.) and in the eye image (macula, etc.) can be assigned to one another. For example, both images may in each case be superimposed to form a total image such that their image boundaries are arranged at a fixed ratio to one another (in the case of environment and retina reflex images of the same size, for example, congruently). This means that the two images can be represented in a common coordinate system, preferably in a coordinate system that is fixed with respect to the device according to the invention. In the total image, distances or relative positions between significant characteristics of the environment image and the eye image can be determined. From the change of the relative position of the significant characteristics with respect to one another in the total image, the change of the orientation of the eye with respect to be environment can be determined.

Likewise, the two images (for example, by means of a correlation method or by rotation and displacement) can be made congruent. From the resulting values (such as correlation factors or angle of rotation and displacement), the change of orientation of the eye with respect to the environment can again be determined.

4.3.3.3 Orientation Device—Environment

An orientation change of the device with respect to the environment can be determined from the change of an image fixed relative to the environment (environment image), for example, of an image taken by a camera fixedly connected with a device, or reflected by the retina or the cornea and detected by a device according to the invention.

For this purpose, for example, two environment images taken at a time interval from one another are compared with one another in the same coordinate system preferably fixed with respect to the device. When the orientation of the device with respect to the environment has changed in the interim, the same significant patterns within the environment image at different points in time have different positions within the coordinate system. This results in the change of orientation. As an alternative, the two images can be made congruent (for example, by a correlation method or by rotation and displacement). From the resulting values (for example, correlation factors or angle of rotation and displacement), the orientation change of the device with respect to the environment can again be determined.

Likewise, the orientation of the device with respect to the environment can also be determined by a comparison of a device image with an environment image in that, for example, both images are viewed in a common coordinate system preferably fixed to the device, and significant structures in the device image and in the environment image are assigned to one another. An orientation of the device relative to the environment can then be determined from the relative position of these structures with respect to one another, for example, of a marker on the device or the geometrical shape of a pair of spectacles, with respect to a significant edge, a pattern, etc. in the environment image.

By a repeated time-shifted ascertaining of such an orientation, an orientation change of the device can also be determined with respect to the environment.

When, in addition, the orientation of the eye with respect to the device is determined, relative-kinematically, an orientation change of the eye with respect to the environment can be determined therefrom.

Likewise, when the orientation of the device with respect to the environment is known, which may be determined, for example, by means of an orientation determining device, and the orientation of the eye with respect to the device is known, relative-kinematically, an orientation of the eye with respect to the environment can be determined.

4.3.3.4 Orientation Eye—Device

By means of an image fixed with respect to the eye (eye image), for example, an image of the retina or of the cornea, in which structures of the eye, such as scars, blood vessels, etc. can be recognized, the orientation of the eye can be determined with respect to the device.

When, in addition, the orientation or change of orientation of the device with respect to the environment is known, together with the orientation or orientation change of the eye with respect to the device, relative-kinematically, the orientation or orientation change of the eye can be calculated with respect to the environment.

4.3.3.4.1 Relative Orientation Eye—Device

4.3.3.4.1.1 Markers

When an image fixed relative to the device (device image), for example, an image in which a marker fixed relative to the device can be recognized, is compared with an image fixed relative to the eye (eye image), for example, an image of the retina or of the cornea, which is obtained, for example, from an active scanning, an orientation of the eye relative to the device can be obtained therefrom. When images are compared which were taken at different points in time, an orientation change of the eye relative to the device can be determined therefrom.

For determining the orientation of the eye relative to the device, a device image and an eye image can be considered in a common coordinate system, preferably in a coordinate system fixed respect to the device (device-fixed coordinate system).

Advantageously, an image reflected by a part of the eye can be used as a device image, for example, the environment reflex image of the retina or of the cornea or a retina reflex image, in which a marker can be recognized which is fixed with respect to the device. Particularly preferably, structures fixed with respect to the device (marker, geometrical shape of the spectacle lens, etc.) within the eye image can be used as a device image, because then the device image and the eye image are already present in the same device-fixed coordinate system or advantageously are already superimposed in the same image.

These images are compared with one another; i.e., certain significant structures within the device image (marker, edges of the spectacle lens, etc.), which may be identified, for example, by means of pattern identification, are assigned to certain significant structures of the eye image (for example, the macula, the pupillary center, etc.), and their position relative to one another is determined.

By means of this relative position, the orientation of the eye relative to the device can be determined.

For example, it may be determined in the device image at which point a marker is situated. In the eye image, it may be determined at which point the macula center and/or pupillary center is situated. By means of this relative position, the orientation of the eye relative to the device can be determined.

The orientation change of the eye relative to the device can therefore be determined when a significant pattern of the device can be recognized in a scanned image of a part of the eye.

For this purpose, for example, a marker may be present on an optical device of a device according to the invention, for example, on a mirror, on a lens, in a hologram, on a spectacle lens in front of the eye, etc., in such a manner that light beams are reflected particularly strongly ("light" marker) or particularly weakly ("dark marker). The marker may, for example, be generated holographically, preferably in a wavelength range not perceived by the eye, for example, in the infrared range. An edge of a spectacle lens, for example, may also be used as a marker.

A detector detects light beams which are reflected by a part of the eye, for example, the thermal radiation of blood vessels of the retina or light reflected by the retina. In an image created therefrom, significant structures of the eye can be detected which are fixed relative to the eye, for example, blood vessels or the macula. In the image, the marker fixed relative to the device is also visible, which is arranged, for example, on a fixed mirror of a detector light-guiding arrangement such that a light beam reflected from the eye, which impinges on the fixed mirror at the point of the marker, is not guided or is guided only very little in the direction of the detector. In the detected image, the marker will then appear dark. From the relative position of the images of at least one significant structure of the eye relative to an image of the marker, the orientation of the structure and thus of the eye relative to the marker and thus to the device can be determined.

Further markers according to the invention and their use respectively are disclosed in the "Marker" section in the "Optical Device" section.

4.3.3.4.1.2 Position of the Device

For determining the orientation of the eye relative to the device, an eye image can be viewed in a coordinate system fixed with respect to the device (device-fixed coordinate system).

For example, a coordinate system fixed to the device may be determined by a neutral position of the detector system. In an eye image viewed in such a coordinate system, certain significant structures (macula center, pupillary center, etc.) may be determined, and their position with respect to the coordinate system may be determined. By means of this position, an orientation of the eye relative to the device can then be determined.

4.3.3.4.2 Relative Orientation Change—Device

Likewise, a change of the orientation of the eye relative to the device can also be determined in that, analogous to an above-described method, at different points in time, one orientation of the eye respectively is determined with respect to the device.

Thus, for example, for this purpose, the relative position of at least one defined significant structure of an eye image, which was scanned at different points in time, can be determined within a device-fixed coordinate system and/or relative to a device image, particularly, for example, a marker. From the change of this relative position between the different points in time of the scanning, a change of orientation of the eye with respect to the device can then be determined.

Likewise, two eye images, which were scanned at different points time, (for example, by a correlation method or by rotation and displacement) can be made congruent. From the resulting values (for example, correlation factors or angle of rotation and displacement), the orientation change of the eye with respect to the device can again be determined.

Full Content Reference to Other Applications, Disclosures

As explained in this specification, the present invention can advantageously be used in connection with the systems, devices and methods described in Published Patent Applications or Applications PCT/EP00/09843, PCT/EP00/09840, PCT/EP00/09841, PCT/EP00/09842, DE 101 27 826, PCT/EP01/05886, DE 196 31 414 A1 and DE 197 28 890 A1. The present invention can also advantageously be used in connection with the application with the title "Information System and Method for Providing Information by Using a Holographic Element" filed by the applicant of this application on Oct. 8, 2001. The entire content of these published patent applications and applications respectively is therefore explicitly included in this application by reference.

Preferred Embodiments

The determination of the position and/or orientation, particularly of the direction of vision, of the eye preferably takes place without being perceived. As a result, it is avoided that the user may be disturbed by virtual points in his field of view.

A device according to the invention is preferably constructed to be portable, particularly in the form of a pair of spectacles. It thereby becomes possible, for example, to also use this device in automobiles, airplanes, etc and in each case determine the direction of vision of the eye.

A projection system according to the invention preferably projects an infrared light beam onto the eye, the diameter of the light beam being very small in comparison with the diameter of the pupil. Preferably, the ocular, particularly the retinal reflex of the beam is detected. In contrast to a prejudice in the state of the art, a light beam with such a small diameter is sufficient for generating a sufficiently reflected beam. When scanning by means of light beams of small diameters, the curvature of scanned parts of the eye advantageously does not play a significant role and especially does not cause any significant distortions of the image.

A device according to the invention preferably comprises a splitter mirror arranged in an infrared light beam, which allows only a small fraction of the infrared light beam to pass and reflects a correspondingly large fraction of the impinging ocular reflex in the direction of a detector device. As a result, light is projected on the same beam path onto or into the eye or reflected from or out of the eye, whereby it can, for example, be ensured that the detector always receives a signal and does not first have to be adjusted to the illuminated point.

A projection system according to the invention preferably projects light in a pixel-type manner with a defined pixel frequency onto the eye. Particularly preferably, a projection system according to the invention modulates the projected light with a frequency higher than the pixel frequency. As a result, it becomes advantageously possible to transmit information within a light beam reflected at a point or pixel, for example, concerning the point in time of the emission or in order to be able to differentiate the light beam from the ambient light.

Preferably, no active illumination of the eye takes place, and the detector system carries out a pixel-type scanning of the ambient light reflected back from the eye and/or of the light emitted by the eye. Advantageously, no projection system is required in this case.

Preferably, a device according to the invention has a surface that can be positioned in front of the eye: the marker areas which reflect an impinging projection beam originating from the projection system completely back in the direction of the detector system, as well as normal areas which guide an impinging projection beam originating from the projection system in the direction of the center of the eye. By means of the marker area, for example, the orientation of the eye can be determined with respect to the marker areas and thereby the device according to the invention.

A device according to the invention preferably determines the position and/or orientation of the eye with respect to its environment in that the detector system detects the retinal structure of the eye as well as also the environment reflex image superimposed thereon, detects the position of the fovea by means of the retina structure and identifies the area of the environment sighted by the fovea by means of a pattern identification.

The device according to the invention preferably detects a representation at least of selected area of the retina and files these in an intermediate memory. For determining a change of the spatial position of the eye, the device according to the invention particularly preferably compares the filed representation with information which the device has obtained from light scanned from the retina and detected during an actual scanning movement. This may advantageously permit a fast comparison.

The device according to the invention preferably comprises a surface having a predefined geometrical shape which can be positioned in front of the eye and by way of which light can be projected from the projection system into the eye, the geometrical shape of the surface being used for determining the relative position of at least one characteristic area of the retina with respect to the optical detector system and/or projection system. Advantageously, no additional markers are required in this case.

Embodiments and Examples of Application

In the following, some of the characteristics or terms indicated in general above will first be explained in detail or by means of embodiments of the present invention. For a better clarity, reference is made in this case to the structuring of the above summary of the invention. It is pointed out expressis verbis that the following specifications have the purpose of illustrating examples and represent no restriction of the characteristics or terms generally specified in the summary. Some preferred embodiments of the present invention will then be indicated.

BRIEF DESCRIPTION OF THE DRAWINGS

FIG. 7b is an enlarged view of the radiator—detector combination from FIG. 7a;

FIG. 16 is a schematic view of an eye in the reference and rotated position as well as an environment;

FIG. 16A is a view of the environment reflex image of the retina;

FIG. 16B is a view of a retina reflex image;

FIG. 16C is a view of an environment reflex image of the retina when the eye is rotated;

FIG. 16D is a view of the retina reflex image when the eye is rotated;

FIG. 16E is a view of the environment reflex image of the retina when the device is rotated;

FIG. 17A is a view of a spectacle lens with a marker in front of an eye;

FIG. 17B is a view of an environment reflex image and a superimposed retina reflex image of the eye from FIG. 17A;

FIG. 17C is a view of the arrangement from FIG. 17A when the eye is rotated;

FIG. 17D is a view of an environment reflex image and a superimposed retina reflex image of the eye from FIG. 17C;

DETAILED DESCRIPTION OF THE INVENTION

A device and a method respectively for determining the position and/or orientation of an eye according to the present invention consist of detecting and analyzing a light signal reflected by a part of the eye by means of a detector system.

Figure 1:
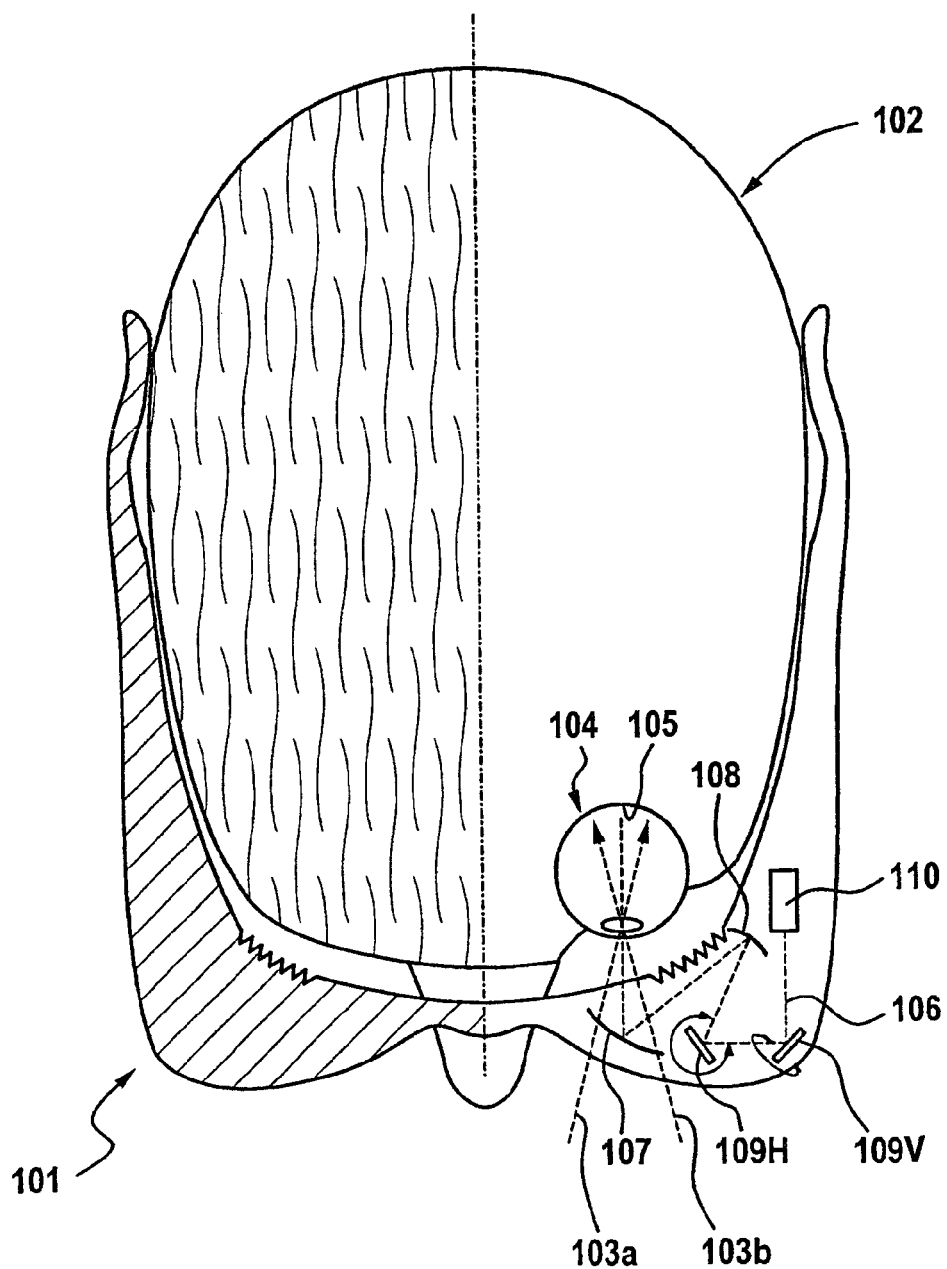
FIG. 1 is a view of an embodiment of the device according to the invention in the form of spectacles.

For a better understanding, this will be explained as an example by means of an embodiment of the present invention. For this purpose, FIG. 1 illustrates a device according to the invention in the form of spectacles 101 on a user's head 102, the right half of the figure representing the top view of the head 102, and the left half of the figure representing a sectional view approximately at the level of the center of the eye. Light beams 103a, 103b ("light signal" in the present embodiment) enter the user's left eye 104 from the environment and are partially reflected on its retina 105 ("part of the eye" in the present embodiment). A light beam 106 reflected at a certain point of the retina impinges on a first fixed concave mirror 107 and is guided by it onto a second fixed concave mirror 108. From this mirror 108, the beam 106 is guided onto a horizontally movable flat mirror 109H and is guided by the latter onto a vertically movable flat mirror 109V. From the vertically movable flat mirror 109V, the beam 106 is guided onto a photo detector 110 which detects the incident beam 106 with respect to its intensity, wavelength or the like (in the present embodiment, "detector system" comprises the photo detector as well as the mirror arrangement). By suitable movements of the flat mirrors 109H and 109V respectively, light beams, which were reflected at different points of the retina, can be sequentially guided into the photo detector 110. In this manner, the retina can be scanned along a predefined movement pattern (scan pattern). From the resulting information, an orientation of the eye can be determined ("Analysis" in the present embodiment).

For a better understanding, the operating method and the technical terminology of the eye will be briefly discussed in the following.

Figure 2:
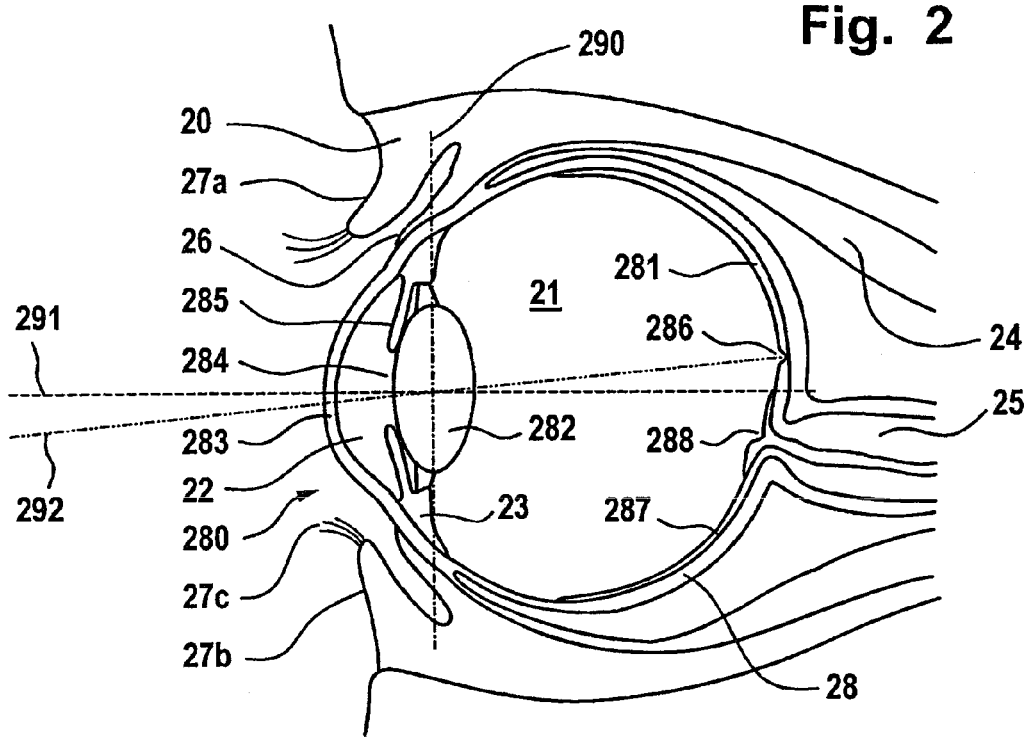
FIG. 2 is a longitudinal sectional view of a human eye.

The eye or the eyeball 280 illustrated in FIG. 2 is moved by the six muscles 24 in the eye socket (orbita) 20 and, as a result, its orientation relative to the skull is adjusted. The upper eyelid 27a and the lower eyelid 27b with the eyelashes 27c change over into the conjunctiva 26 which closes off the space between the orbita 20 and the eyeball 280.

The eyeball 280 consists of a transparent, approximately spherical vitreous body 21, on which a deformable lens 282 rests in the front in the direction of vision, the focal point of the lens 282 being changeable by the tensioning and relaxing of ciliary muscles 23 arranged on the circumference. Directly in front of the lens 282, an aperture (iris) 285 consisting of a colored material is arranged whose pupil 284 can be changed in its diameter in a muscular manner.

The rearward part of the vitreous body is surrounded by the sclera 28 whose interior side is covered by the choroid 287. Between the vitreous body 21 and the choroid 287, the retina 281 is situated which is supported by the vitreous body and supplied with blood by the choroid. The retina comprises extremely light-sensitive rods for the scotopic vision (in twilight) as well as less light-sensitive cones for the photopic vision (color vision in daylight). The so-called yellow spot (macula) with the fovea centralis 286—the region with the sharpest vision—with a very high cone density is situated inside the retina. The blind spot 288 is situated in another region, which blind spot 288, the optic nerve 25 leads into the retina and where no image information can be received.

The forward part of the vitreous body is surrounded by the transparent cornea 283 such that the anterior chamber 22 of the eye is formed between the cornea and the iris and is filled with a transparent liquid. At its circumference, the cornea changes over into the sclera.

In the optical system of the eye, light which is incident in parallel in the case of an emmetropic relaxed eye is essentially focused through the cornea on the retina. By changing the refraction of the lens 282, object at different distances are imaged sharply. In the following, the mid-perpendicular onto the principal plane 290 of the lens 282 is called the optical axis 291 of the eye 280. In contrast, the straight line through the pupillary center and the fovea centralis 286 is defined as the direction of vision 292 because, as a rule, a human being will focus his eye on a point to be viewed such that this point is imaged in the region of the sharpest vision. While, in the normal case, the optical axis 291 and the direction of vision or visual axis 292 hardly deviate from one another, there is definitely the possibility that the fovea centralis is not situated opposite the pupil. The eye then seems to be strabismal.

Concerning 1.2 Passive Scanning

From the polyspectral ambient light, light beams of particularly suitable wavelengths can be filtered out, such as light in the green-yellow range of the sharpest vision between 500 nm and 600 nm in order to thus be able to detect the macula particularly well, or light in the range of approximately 750 nm, at which the reflectivity of the retina is the highest.

Concerning 1.3.1.1 Amplitude Modulation

Figure 3A:
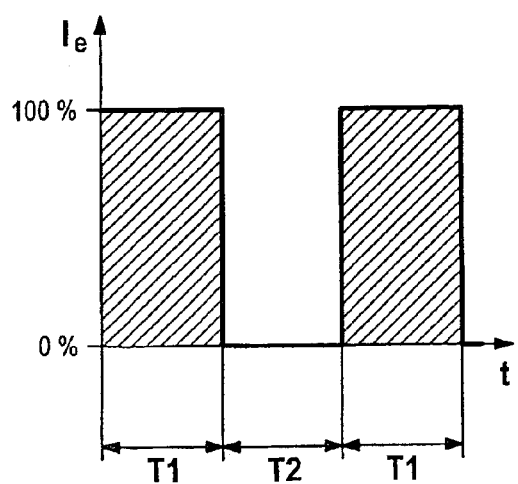
FIG. 3a is a view of a course of the radiant intensity $I_e$ over the time.

Amplitude modulation is a modulation at which at least one of the above-indicated characteristic quantities in different time segments or at different points in time each have certain values. As an example, FIG. 3a shows the radiant intensity $I_e$ of an actively beamed-in light over the time, which, in a first time period T1, has a reference value of 100% and, in a subsequent second time period T2, has a value of 0%, periods T1 and T2 following one another periodically. When such an actively beamed-in light, together with the ambient light, is reflected at a point of the retina, and the radiant intensity of the entire light beam reflected at this point is detected in a detector, approximately exactly the actively beamed-in light without ambient light fractions is obtained from the difference of the light intercepted in period T1 and of the light intercepted in period T2.

Concerning 1.3.1.2 Frequency Modulation

Figure 3B:
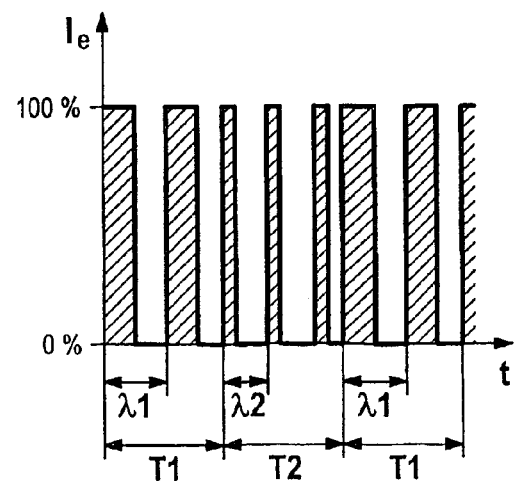
FIG. 3b is a view of another course of the radiant intensity $I_e$ over the time.

The change of a periodicity of at least one of the above-indicated characteristic quantities is called frequency modulation. Again as an example, FIG. 3b shows the radiant intensity $I_e$ of an actively beamed-in light over the time, which is beamed in in a first time period T1 in a pulsed manner with a period λ1 and in a subsequent second time period T2 in a pulsed manner with a period length λ2≠λ1. When such an actively beamed-in light, together with the ambient light, is reflected at a point of the retina and detected in a detector, it can be determined by means of the period λ1 or λ2 whether the light beam was reflected during period T1 or period T2. Generally, for example, the periodicity between a not shown point in time TA and a not shown point in time TE can be changed according to a predefined relation; thus, for example, decrease in a linear fashion between TA and TE. Then, from the periodicity of the reflected and detected light beam, the point in time between TA and TE can be determined at which the beam was emitted. This permits, for example, a propagation time measurement and thus, for example, when the geometry between the detector system or projection system is known, the determination of the distance between the reflecting point of the eye and the detector or projection system as a product of the speed of light and of the propagation time. Likewise, it makes it possible to differentiate between actively beamed-in light and ambient light.

One or more characteristic quantities of the actively beamed-in light beam may simultaneously or sequentially be amplitude-modulated and/or frequency-modulated. In FIG. 3b, the period length (frequency modulation) as well as the pulse width (pulse code modulation) is changed between period T1 and period T2.

Concerning 1.3.2 Adaptation of the Active Luminous Intensity

In contrast to the passive scanning, the active scanning has the advantage that it can be ensured that always light of a sufficient intensity is reflected from the eye in that actively a correspondingly large amount of light is beamed in. For example, the radiant intensity of the radiator, which actively emits the light, can be adapted such that the detector can sufficiently clearly detect the resulting reflected light beam. When the detector can no longer detect the actively beamed-in and reflected light beam, the light intensity can be increased correspondingly. When the detector records a very high light intensity of the actively beamed-in and reflected beam, the light intensity is correspondingly reduced. The orientation of the eye can therefore also be determined in darkness (virtual-reality spectacles, night vision device, etc.) or under considerably changing light conditions (driving through a tunnel, etc.).

Concerning 1.3.3.1 Point-Focal Illumination

According to the invention, a light beam can be emitted from a radiator, for example, a laser and can be guided by means of a projection light-guiding arrangement such that successively, i.e, sequentially, different points on the part of the eye are illuminated. This can be carried out, for example, by means of a device which is constructed analogously with respect to the device illustrated in FIG. 1, the detector 110 being replaced by a radiator (reversibility of the beam path). By means of a corresponding movement of the two flat mirrors 109H or 109V, the light beam emitted by the radiator is then sequentially guided to different points of the retina 105. In this case, the end point of the light beam on the eye follows a movement pattern (projection movement).

Figure 4:
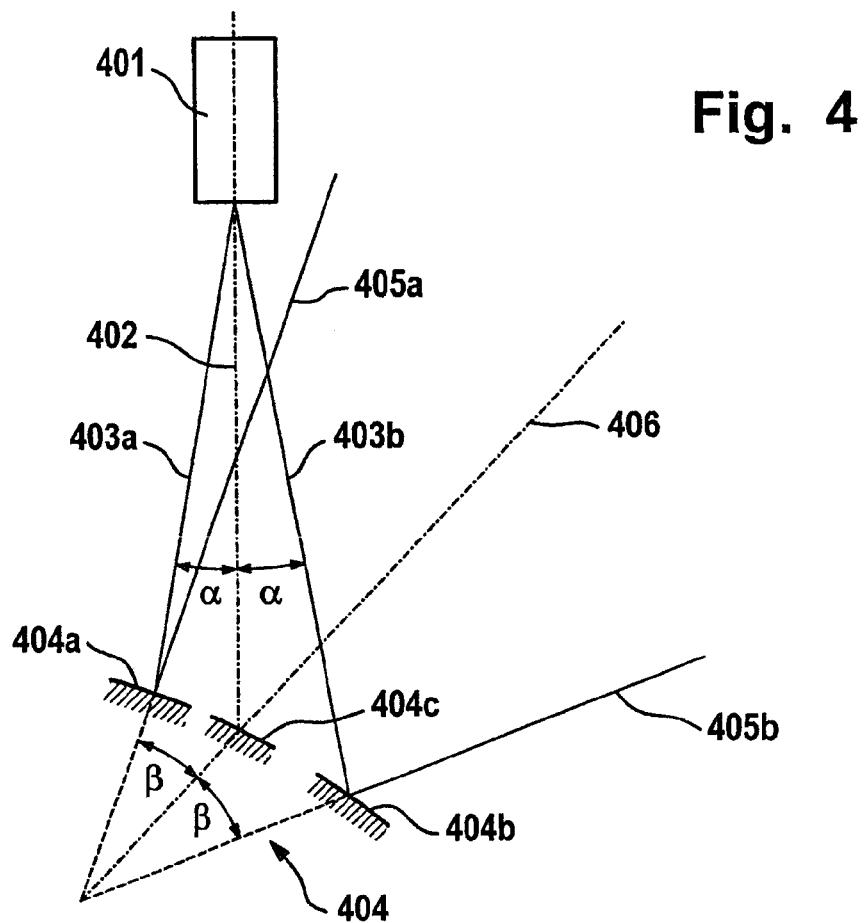
FIG. 4 is a view of a controllable laser as the radiator.

As an alternative, the radiator itself can guide the emitted light beam onto different points of the part of the eye. For example, a controllable laser can emit the emitted light beam to a curved or multipart mirror such that, in each case, a certain mirror area is impinged upon at a certain angle. The mirror areas are mutually inclined by different angles, so that a light beam impinging at the same angle with respect to the entire mirror is deflected on different mirror areas into different directions. For this purpose, FIG. 4 shows a controllable laser 401, which can deflect a light beam maximally by the angle α from the principal axis 402. In the case of a maximal deflection a in the plane of projection, the marginal rays 403a and 403b respectively are obtained. These are reflected to the corresponding mirror areas 404a and 404b respectively of a mirror 404, these mirror areas being appropriately inclined with respect to one another. With respect to the principal ray 406 reflected on a mirror area 404c inclined with respect to the mirror areas 404a and 404b respectively, the reflected marginal rays 405a and 405b respectively have an angle β which is greater than the original angle α. In this manner, also by means of a radiator which can only implement a small deflection of the emitted beam, sufficiently large scanning areas can be implemented. The surface of the mirror 404 with the corresponding mirror areas 404a, 404b and 404c respectively is geometrically obtained from the corresponding angles and distances.

Concerning 1.3.3.1.1 Detection of Light from the Entire Pupil

Figure 18:
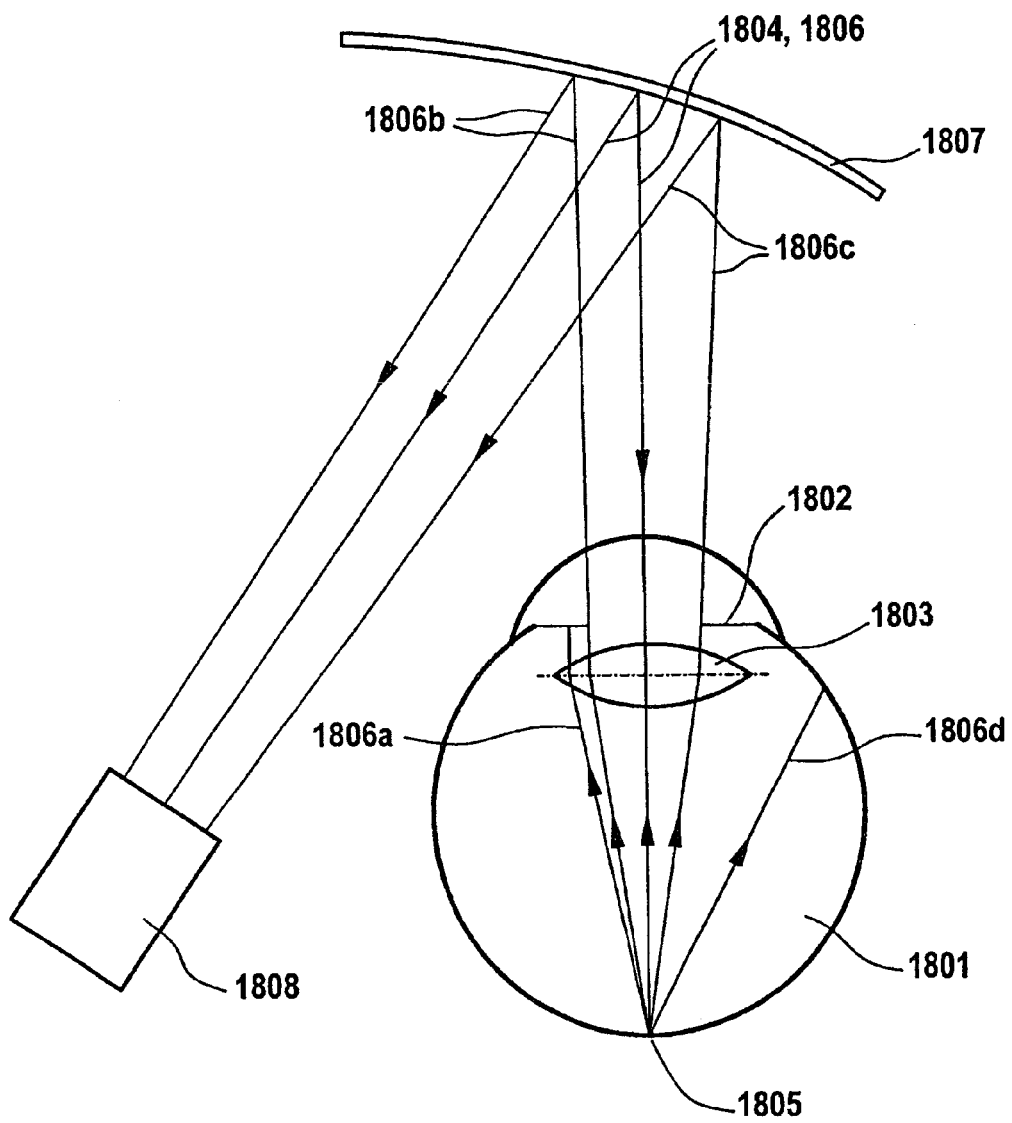
FIG. 18 is a view of a reflected principal ray and of marginal rays.

FIG. 18 illustrates a light beam 1804 which is beamed into an eye 1801 having a pupil 1802 and a lens 1803 and which has a very small diameter. This light beam is beamed back (reflected or scattered) at a point 1805 of the retina of the eye 1801, for the most part as a principal ray 1806 which, in the illustrated case, accidentally corresponds to the beamed-in light beam 1804. This special configuration is chosen here only for the purpose of a clearer representation and does not restrict the embodiments. The entire light 1804 is not reflected back in this direction in parallel as a main ray 1806, but a portion is also reflected in other directions as rays 1806a, 1806b, 1806c, 1806d, resulting, for example, in a lobar intensity distribution of the beamed-back light around the principal ray. A portion of these light rays reflected in another than the reflection direction exits through the pupil 1802 from the eye and extends approximately coaxial with respect to the reflected principal ray 1806. For this purpose, the two marginal rays 1806b, 1806c are outlined which just barely still pass through the pupil 1802. Rays 1806a, 1806d are reflected such that they no longer pass through the pupil 1802. A detector light-guiding arrangement 1807 (in a simplified manner illustrated as a mirror) is constructed such that also these marginal rays are guided to a detector 1808 and are detected by it, whereby the detected quantity of light is advantageously increased.

Concerning 3.2.1 Mirrors

In a preferred embodiment, the detector light-guiding arrangement comprises one or more mirrors, whose orientation to one another, to the eye whose orientation is to be determined, and to the detector can be adjusted such that the light beams which were reflected at certain points of the eye are sequentially guided to the detector.

The orientation of the movable mirrors can be controlled such that a desired movement pattern can be scanned. As illustrated, for example, in FIG. 1, two flat mirrors may be present for an, as a rule, two-dimensional pattern (such as a grid, a spiral or the like,) which flat mirrors can be moved about two mutually different axes. As an alternative, a wobble mirror, for example, can also be used.

As illustrated in the example of FIG. 1, in addition to the movable mirrors, fixed mirrors may also be present. A first fixed mirror may, for example, be a semitransparent mirror which allows light to pass in the direction onto the eye and deflects light exiting the eye. As a result, it becomes possible to arrange the detector outside the visual field of the eye. Additional fixed mirrors, as also illustrated in FIG. 1 by means of examples, may be arranged such that the detector and/or the movable mirrors can be arranged in a particularly favorable manner, for example, outside the field of vision of the eye and/or at a suitable point of the device.

Concerning 3.3.1 Radiator

Advantageously, at least one of the physical quantities of the light emitted by the radiator can be adjusted. For example, a radiator may emit light beams having a certain time-related pattern with respect to intensity, wavelength or the like, as outlined by an example in FIGS. 3a, 3b.

Concerning 3.3.3 Projection Light-Guiding Arrangement

In order to guide light emitted by the radiator onto the region of the eye by which it is to be reflected and subsequently is to be detected in the detector system, a projection light-guiding arrangement may be present into which light enters that was emitted by the radiator and which guides this light onto the desired region.

In particular, the detector light-guiding arrangement itself may form part of the projection light-guiding arrangement in that the light emitted by the radiator enters in the opposite direction parallel into the beam path in front, in or behind the detector light-guiding device.

Figure 5:
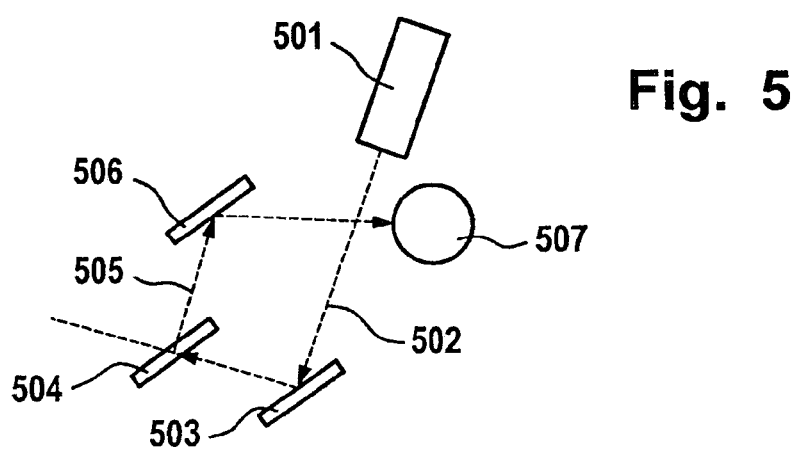
FIG. 5 is a view of an arrangement of the radiator and the detector with a common light-guiding device.

As an example, FIG. 5 illustrates a radiator 501 which emits a light beam 502. The latter is guided from a mirror 503 onto a semitransparent mirror 504 which allows the light beam 502 to pass as unchanged as possible. A semitransparent mirror may be a splitter mirror which preferably allows light to pass light through the mirror as unchanged as possible in one direction and reflects light as completely as possible in the opposite direction. The light beam 502 then enters into a detector light-guiding arrangement, as formed, for example, in FIG. 1, by the movable flat mirrors 109V, 109H and the two concave mirrors 107, 108. From this detector light-guiding arrangement, the light beam is guided and/or focused onto a certain region of the eye, is reflected at this region and, on the same path, as a reflected light beam 505, impinges again on the semitransparent mirror 504. The latter reflects a fraction of the impinging light beam 505 that is as large as possible onto another mirror 506 which guides the light beam 505 reflected on a part of the eye into a detector 507, where at least one characteristic quantity of this light beam is detected.

Embodiments Concerning the Optical Device

For clarifying the above-indicated characteristics by means of the figures, several conceivable embodiments of the optical device according to the present invention are described by means of a preferred embodiment in the form of spectacles. The invention is not limited to spectacles; it may, for example, also be arranged in a frame wearable on the head, a helmet, or the like. Likewise, it may, for example, also be fastened on a stationary apparatus which uses the information concerning the orientation of the eye supplied by the device with respect to the orientation of the eye, for example, on an apparatus for laser surgery or the like. Likewise, it may be fastened on an object which is movable relative to the environment and relative to the carrier, as, for example, a portable electronic notebook, a laptop or the like. Furthermore, in the case of the described embodiments, the retina is used as a reflecting part of the eye. As described above, other parts of the eye (cornea, iris) can also be used.

Figure 6:
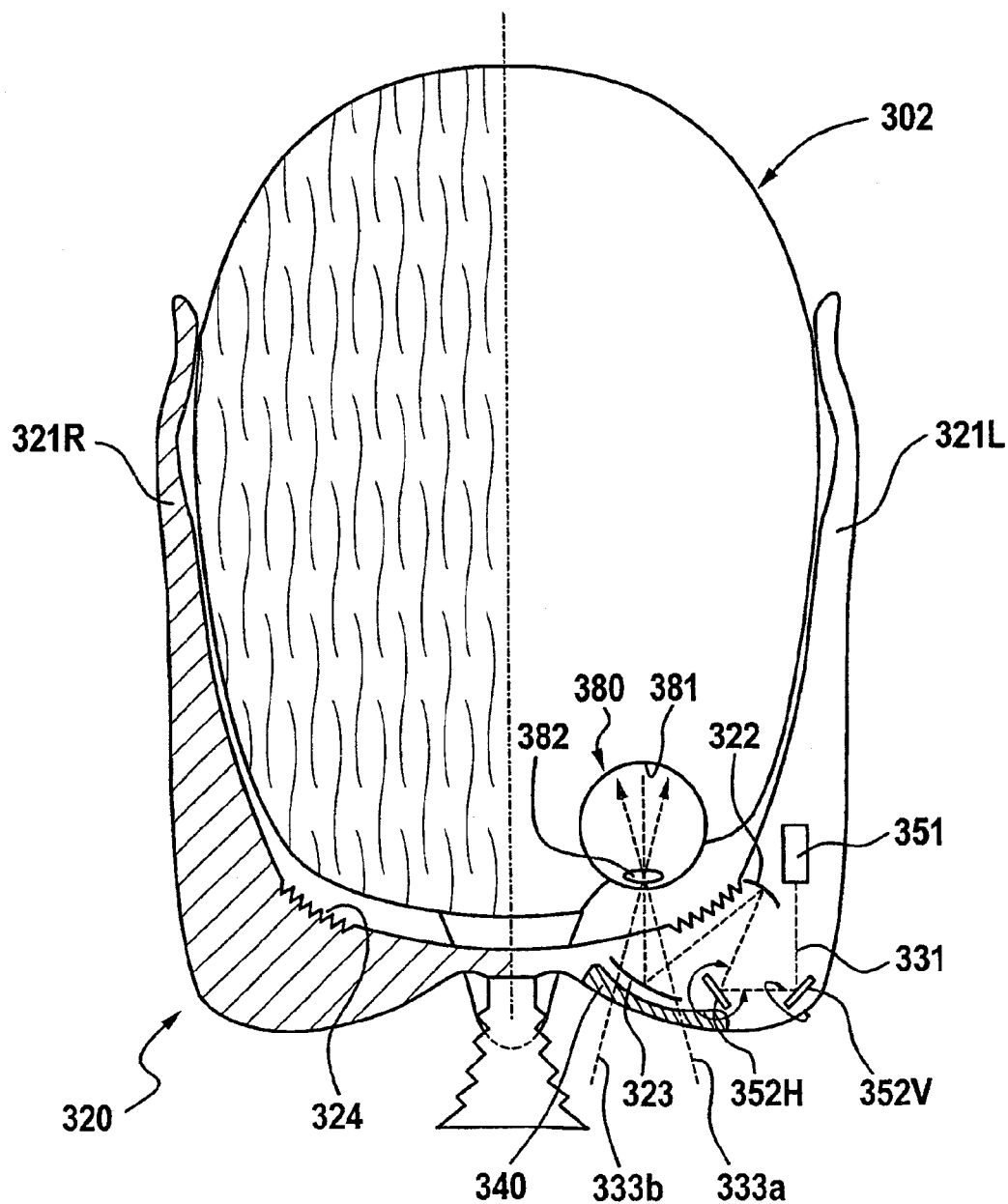
FIG. 6 is a view of an embodiment of the device according to the invention in the form of spectacles.

In FIG. 6, the user 302 is wearing a device according to the invention in the form of spectacles 320 having a left and a right bow 321L and 321R respectively. The left half of the figure is a top view; the right half is a sectional view extending through the left bow 321L.

Light beams 333a, 333b are incident in the eye 380 from the environment and are focused from its cornea and lens 382 onto the retina 381. The retina reflects these beams partially such that the latter exit from the eye 380 again through the lens 382. Depending on the wavelength of the incident light, the reflectivity of the retina amounts to approximately 0.2-10%. A beam 331 reflected in this manner is guided by a first semitransparent concave mirror 323, which allows light to pass as unchanged as possible in the direction onto the eye and almost completely reflects light exiting from the eye, and by a second concave mirror 322 onto a horizontally movable first flat mirror 352H, from the latter to a vertically movable second flat mirror 352V and from the latter to a photo detector 351. Depending on the position of the two flat mirrors 352H, 352V, a specific light beam 331, which was reflected at a certain point of the retina, is guided into the detector 351 and is guided in the latter by means of a focusing device, such as a converging lens, onto a photocell which detects the intensity of the light beam. Intensity of the light beam always applies to a suitable quantity of the reflected light beam measurable by a detector, such as the intensity of irradiation, the radiance, the light intensity, the brightness or the like. By means of a corresponding movement of the two flat mirrors, those light beams are therefore sequentially detected which were reflected at points along a corresponding trajectory on the retina; the environment reflex image is scanned as a scanning element sequence.

For example, in the case of a fixed first flat mirror 352H and a second flat mirror 352V uniformly rotated about its horizontal axis, the scanning elements of a vertical straight line are point-focally scanned on the retina. In the case of a first flat mirror 352H uniformly rotated about its vertical axis and a fixed second flat mirror 352V, horizontal straight lines are point-focally scanned on the retina. In a preferred embodiment of the present invention, the two flat mirrors are sinusoidally moved up and down or back and forth, so that the curve scanned on the retina 381 may comprise circles (in the case of the same amplitude in both mirrors), ellipses (in the case different amplitudes in the two mirrors), spirals (in the case of increasing amplitudes in the two mirrors) or other suitable curves.

In a further embodiment, the two flat mirrors 352H, 352V are replaced by a wobble mirror movable about at least two axes, which is arranged such that it guides light beams from the second concave mirror 322 into the photo detector 351. By a corresponding controlling of the wobble mirror, scanning element sequences along arbitrary trajectories on the retina can also be detected by the photo detector 351.

A light trap 324 prevents that light impinges on the eye and/or the mirrors from undesired directions of incidence.

Instead of the first concave mirror 323, the spectacle lens 340 can be reflectively coated such that it reflects at least the light beams reflected by the eye as completely as possible. In order to, also in the case of rotated eye positions, appropriately deflect light beams reflected by eye to the second concave mirror 322, the reflective surface of the spectacle lens facing the eye should have a corresponding shape. To this extent, reference is made to the full content of PCT Application "Information System and Method for Providing Information by Using a Holographic Element" filed by the same applicant on Oct. 8, 2001. The reflective surface of the desired shape can preferably be emulated by means of a correspondingly constructed holographic coating of the spectacle lens 340.

Instead of the different reflective arrangements described here and in the following (flat mirrors, wobble mirrors or concave mirrors, reflective surfaces, holographic coatings, etc.), in embodiments of the present invention, all other known optical refraction or reflection mechanisms, for example, electro-holographic mechanisms or the like, can also always be used for guiding the light beams from the radiator to the eye or from the eye to the detector.

In the case of a device for the active scanning, a radiator is additionally present which emits light, such as a laser, an infrared lamp, a light emitting diode or the like. In an embodiment, the photo detector 351 is arranged in the center of a radiator. Thus, for the projection of light onto the eye, the same devices (flat or wobble mirror 352H, 352V; second concave mirror 322; first concave mirror 323 or reflectively coated spectacle lens 340 or holographically coated spectacle lens 340) and thus the same beam path is/are used as for the detection of the reflected light beams. Such an arrangement has the advantage that possibly present systematic defects as a result of deviations of the mirror surfaces or the like are identical in projection and scanning. When the projection system is used, in addition or as an alternative, for the projection of signals onto the retina, the correlation between the scanning point sequence on the retina detected by the photo detector 351, which may, for example, be the environment reflex image of the perceived image in the eye, and the projected-in information which may, for example, be a virtual marker of an object in this image, is not impaired by these systematic defects. Furthermore, the common use of the devices reduces the weight of the optical device, and it is ensured that light emitted by the radiator also always returns at least partly to the detector.

As an alternative, in a (not shown) embodiment of the present invention, an additional second arrangement of a flat or wobble mirror, a second concave mirror and a first concave mirror or a reflectively coated spectacle lens or holographically coated spectacle lens analogous to one of the above-described embodiments may be present where, instead of the photo detector 351, a radiator is present, so that reflected light is detected by the above-described arrangement with the detector 351 and simultaneously can be beamed into the eye by the second arrangement.

Figure 7A:
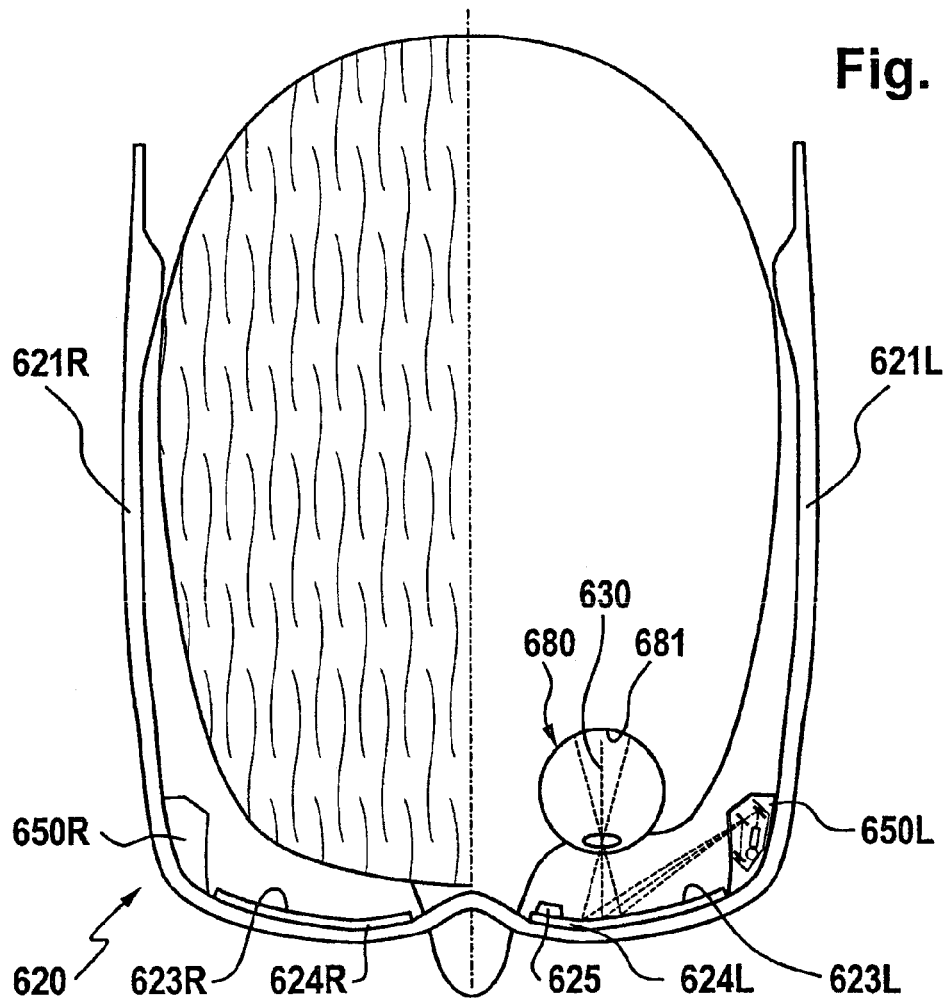
FIG. 7a is a view of an embodiment of a device according to the invention in the form of spectacles.

As an alternative, for the active scanning, one of the embodiments described in the following by means of FIGS. 7a, 7a can be used.

Figure 7B:
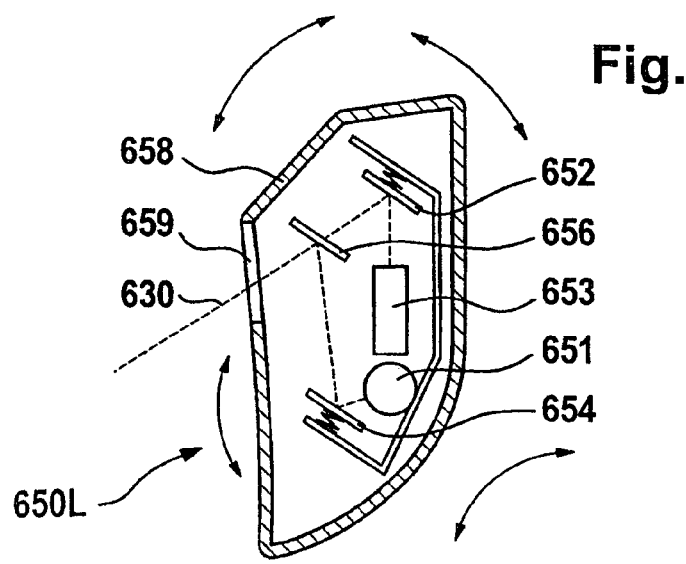

FIG. 7b of a detail illustrates a combined projection and detector system 650L, which is arranged between the left spectacle lens 624L and the left bow 621L. Naturally, this or another embodiment of the present invention may also always as an alternative or in addition be analogously arranged on the right side, in this case, therefore between the right spectacle lens 624R and the right bow 621R. In the present embodiment, the left spectacle lens 624L, on the side facing the eye, is provided with a holographic coating 623L which, as described above, emulates a reflection surface or focusing surface.

The combined projection and detector system 650L comprises a closed-off housing 658 with a light-transmitting window 659. Although, as a result, light beams can enter into the housing and exit from the housing, disturbing foreign matter, such as dust or the like, can be prevented from entering. A radiator 653 and a photo detector 651 are arranged in the housing 658. A light beam 630 emitted by the radiator 653 impinges on a first wobble mirror 652 which, by means of a suitable drive, is positioned such that it guides the light beam by means of a splitter mirror 656 such onto the holographic coating 623L that the light beam is reflected from there onto a desired point on the retina 681 of the eye 680. From this point, the beam 630 is reflected at least partially on the same path back onto the holographic coating 623L and, from the latter, on the same path onto the splitter mirror 656. The splitter mirror 656 guides a part of the arriving beam 630 onto a second wobble mirror 654 which, in turn, by means of a suitable drive, is positioned such that it deflects the beam 630 into the photo detector 651 which scans the beam 630.

In an advantageous embodiment, the splitter mirror 656 is very reflective on the side facing the second wobble mirror 654, so that a percentage of the light beam 630 reflected back from the eye, that is as high as possible, is guided into the photo detector 651.

Advantageously, a marker 625 is mounted on the spectacle lens 624L. This marker can, on the one hand, be used for defining a reference value with respect to the light conditions and the reflectivity of the individual components in the beam path. For this purpose, by means of the first wobble mirror 652, the light beam 630 with a known intensity is guided onto the marker 625 and is partially reflected back by it into the opposite direction. For this purpose, the surface of the marker 625 facing the projection and detector system 650L may have a corresponding construction, for example, a fully reflective construction. The reflected beam 630 is deflected on the splitter mirror 656 onto the second wobble mirror 654 and by the latter into the photo detector 651, where the intensity is recorded and is defined as a reference value, for example, for a 100% reflection. It thereby becomes possible to adapt the optical device also to changing light conditions.

In the case of the present invention, the radiator and/or the detector can always be replaced by a light outlet or light inlet device, which is arranged instead of the light outlet or light inlet opening of the radiator or detector and is connected in a light-guiding manner with a suitable optical wave guide, particularly a glass fiber cable or the like, which, on its other end, is in turn connected in a light-guiding manner with a radiator or detector. As a result, the radiator or detector can advantageously be arranged at any point away from the light guiding arrangement, for example, on the belt of the wearer of a device according to the invention in the form of spectacles, so that the weight of the projector and/or photo detector does not affect the spectacles.

Concerning 4.1 Detected Image

According to the invention, for the determination, points along a trajectory can always be scanned sequentially, i.e., successively. The result is a sequence of scanning points to which, for example, by means of the position of the detector light-guiding arrangement, certain coordinates (such as abscissa x and ordinate y; radius R and polar angle φ) and values for the physical quantity can be assigned. In addition, a distance to the detector can be assigned to each point, for example, on the basis of a measured propagation time and/or focusing and/or interference, so that a relation "physical value (x,y)" or "physical value (x,y,z)" is obtained as a "picture".

For a better understanding, for example, in the arrangement in FIG. 1, an x-value can be assigned to each position of the horizontally movable flat mirror 109H, and a y-value can be assigned to each position of the vertically movable flat mirror 109V. For example, the radiant intensity $I_e$ or brightness of a light beam detected by the detector 110 in this position of the detector light-guiding arrangement, which light beam was reflected at a point of the retina 105, can be quantitatively determined as the physical quantity. When, successively for different positions of the two flat mirrors, the brightness of an incident light beam is determined and stored, a quantity of value triplets (x, y, $I_e$) is obtained which result in a curve in an x-y coordinate system. By means of a corresponding analog-to-digital conversion, specific brightness or gray-scale values can be assigned to the individual points of the curve. In addition, the propagation time and thereby the distance z of the reflecting point from the detector can be determined, for example, by means of a frequency-modulated light beam. A quantity of value tupels (x, y, z, $I_e$) is then analogously obtained which result in a scanning point curve in an x-y-z coordinate system.

In the case of a finer scanning, i.e., for example, smaller steps between the individual positions (x,y) of the flat mirrors, the curve results in an increasingly sharper two-dimensional or three-dimensional "picture" of the part of the eye on which the light beams were reflected.

Concerning 4.2. Detection 4.2.1 Rough Determination of the Pupillary Center

Figure 8:
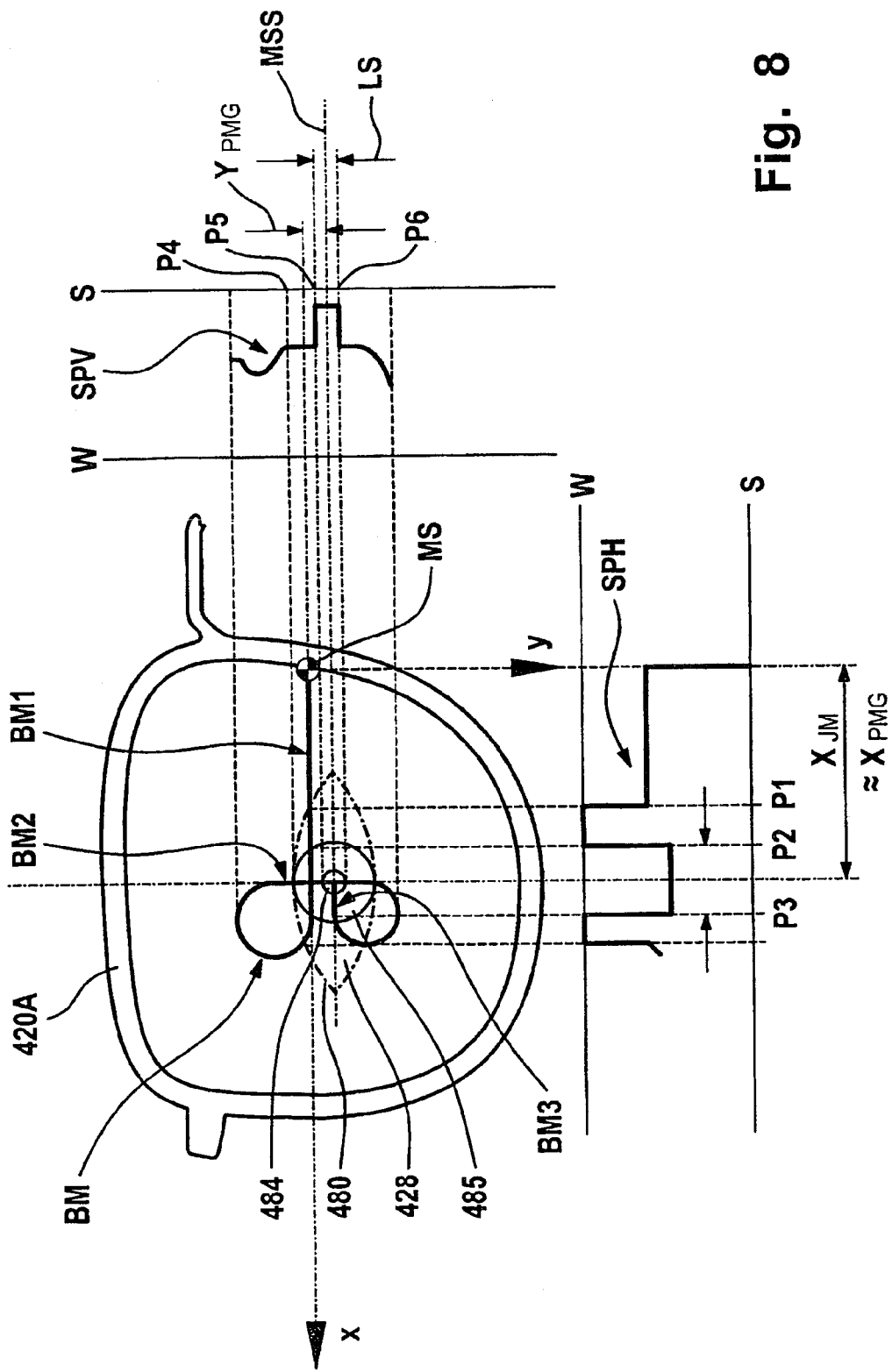
FIG. 8 is a view of a movement pattern for determining the pupillary center.

A characteristic feature of the eye is the pupillary center which, for example, together with the fovea centralis, defines a direction of vision of the eye. By means of FIG. 8, a rough determination of the pupillary center with respect to the device 420A according to the present invention is explained. FIG. 8 is a top view of the image of an eye 480 with the sclera 428, the iris 485 and the pupil 484 behind a spectacle frame 420A.

A plane coordinate system (MS, x, y) is defined for the spectacle frame 420A, with respect to which coordinate system the pupillary center ($x_{PMG}$, $y_{PMG}$) is determined. In this case, a marker MS on the spectacle frame is selected as the origin, the horizontal x-axis and the y-axis perpendicular thereto extending through the marker. The x-axis is advantageously situated approximately at the level of the pupil.

First, as a result of a corresponding movement of the detector mirrors (see "Optical Devices" section), a sequence of points along a first straight line BM1 on the x-axis is actively or passively scanned. The brightness SPH of the scanning elements along this straight line changes at the transition of the scanning beam from the face to the sclera at point P1 to a higher value W ("white"), at the transition from the sclera to the iris at point P2 to a lower value and at another transition from the iris to the sclera at point P3 back to value W. The geometric mean of the x-coordinates of points P2 and P3 is defined as the preliminary x-coordinate $x_{JM}$ of the pupillary center.

Subsequently, a sequence of points along a second straight line BM2, which extends parallel to the y-axis through the point ($x_{JM}$,0) and thus always through the pupil, is actively or passively scanned. The scanning beam preferably changes along a three-quarter circle from the straight line BM1 to the straight line BM2 in order to minimize the oscillation excitation of the device. The brightness SPV of the scanning elements along the second straight line BM2 changes during the transition from the iris to the approximately black pupil at point P5 approximately to a lower value S characteristic of an individual pupil and, during another transition from the pupil to the iris at point P6, again to a higher value. The geometric mean between the y-coordinates of points P5 and P6, between which the scanning beam supplies approximately a, for example, empirically determined characteristic brightness value S, is determined as the y-coordinate $y_{PMG}$ of the pupillary center.

Finally, a sequence of points along a third straight line BM3 is actively or passively scanned, which straight line extends parallel to the x-axis through the point (0,$y_{PMG}$) and thus always through the pupil. The scanning beam preferably changes along a three-quarter circle from the straight line BM2 to the straight line BM3 in order to minimize the oscillation excitation of the device. The brightness of the scanning elements along the third straight line BM3 changes analogously to the second straight line during the transition from the iris to the approximately black pupil approximately to a lower value S and, during another transition from the pupil to the iris, again to a higher value. The geometric mean between the x-coordinates of the points, between which the scanning beam supplies approximately the brightness value S, is determined as the x-coordinate $X_{PMG}$ of the pupillary center.

By means of above-described methods, an appropriately designed analysis device reliably determines the position ($x_{PMG}$,$y_{PMG}$) of the pupillary center with respect to the spectacle frame 420A and stores these data, so that, for example, the methods described in the following can be used starting from the found pupillary center by which the scanning device is correspondingly readjusted (? There seems to be a word missing in the German.)

Should the expected brightness courses not be recorded during the scanning along one of the three straight lines BM1, BM2 or BM3 because, for example, the eye was closed by the lid, the analysis device will recognize that the determination has failed and will repeats at least the failed scanning steps until a faultless determination of the pupillary center has been carried out successfully and/or will report the failing of the determination, from which it can, for example, be concluded, that a blinking is taking place. It can thereby simultaneously be ensured that the eye is open at the point in time of the determination of the pupillary center and, for example, information can also be projected into the eye or the retina can be scanned.

In addition, for example, the distance of point P2 to the detector can be determined and thereby approximately the three-dimensional position of the pupillary center relative to the device according to the invention or to the detector can be determined.

4.2.2 Precision Determination of the Pupillary Center

A precision determination of the pupillary center can be carried out which will be schematically explained in the following by means of FIG. 9. This precision determination can advantageously be carried out after the position of the pupillary center has been approximately determined by means of the above-described rough determination.

Figure 9:
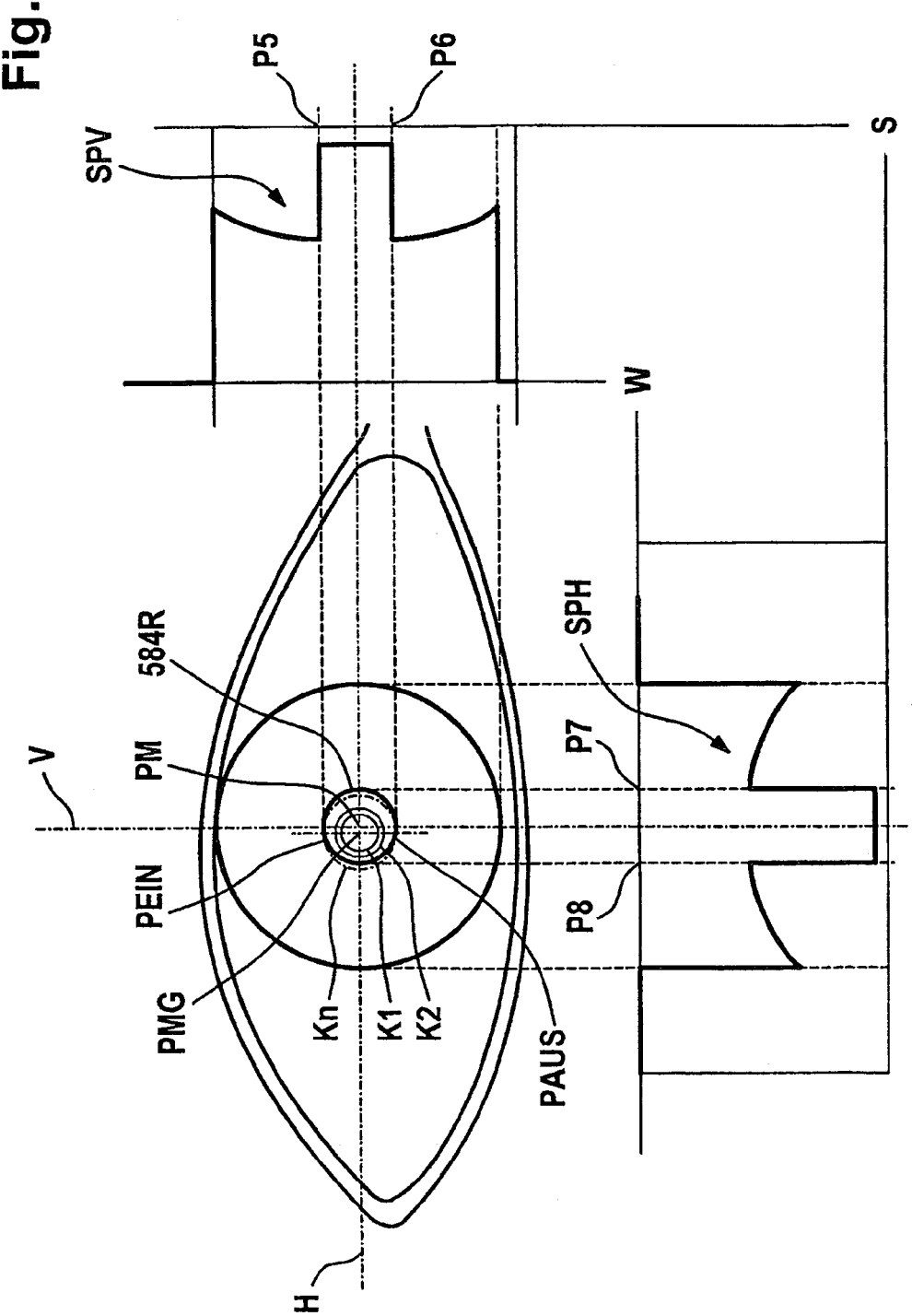
FIG. 9 is also a view of a movement pattern for determining the pupillary center.

FIG. 9 is a top view of an eye with a horizontal line H and a vertical line V perpendicular thereto, which both extend through the (exact) pupillary center PM.

During an active or passive scanning along these lines, approximately the brightness sequences SPH illustrated on the bottom or on the right with respect to the horizontal line H or SPV with respect to the vertical line V are obtained. In this case, the brightness value decreases during the transition from the white sclera to the colored iris from a value W characteristic of the sclera and falls during the transition from the iris to the black pupil at points P7, P8 or P5, P6 approximately to a value S characteristic of the pupil.

When the pupil is now successively scanned along concentric circles K1, K2, . . . Kn around the previously roughly determined pupillary center PMG, the scanning along the circles which are situated completely inside the pupil always results approximately in a constant brightness value S over the entire circumference of the circle; the scanning along the circles which are situated completely outside the pupil always results approximately in a constant brightness value W along the entire circumference of the circle.

The radius r1 of a first circle K1 around the roughly determined pupillary center PMG is selected such that the circle K1 is situated completely within the pupil. For this purpose, the starting value for the radius r1 is used as the beginning, and the brightness values along the pertaining starting circle are compared with the reference value S. Subsequently, the radius is reduced until the brightness values at no point significantly deviate from S. As an alternative, an always sufficient constant maximum radius can also be defined. Then, concentric circles K2, . . . Kn around the roughly determined pupillary center are scanned, the radius ri of each circle Ki being greater than the radius r(i−1) of the preceding circle K(i−1)—until the brightness values along a circle Kn between points PAUS and PEIN on the circumference of the circle Kn are significantly greater than the reference value S. In this case, the roughly determined pupillary center PMG is displaced along the mid-perpendicular onto the secant through points PAUS and PEIN, for example, by the difference of the radii rn and r(n−1). If the points PAUS and PEIN are (approximately) identical, the pupil is completely situated inside the circle Kn. Then the radius rn is reduced until, at least on a partial area of the circumference of the circle Kn, the brightness values no longer significantly deviate from the reference value S, and the process is continued.

The above-described method can be repeated several times, the difference of the radii of successive circles, in contrast to the preceding process pass each being appropriately reduced and a circle with the radius of circle K(n−1) being selected as the first circle K1, which was still completely inside the pupil in order to thereby displace the pupillary center PMG iteratively into the exact pupillary center PM. When in this case, the difference of the radii falls below a predetermined value, the device according to the invention stops the process and considers the found pupillary center PMG as being determined sufficiently exactly.

In the case of the above-indicated method, ellipses can be scanned instead of circles in order to take into account the distortion of the round pupil in the case of a distortion of the eye. Analogous to the above method, a first circle which is situated completely outside the pupil can be used as the beginning and the radii of the following circles are constantly reduced.

Analogously to the above method, the macula on the retina can also be determined. In the following, this will be described by means of FIGS. 10 and 11 respectively. In this case, first a pupillary center determined according to one of the above methods can be assumed to be the starting point for the macula center.

4.2.3 Rough Determination of the Center of the Macula

Figure 10:
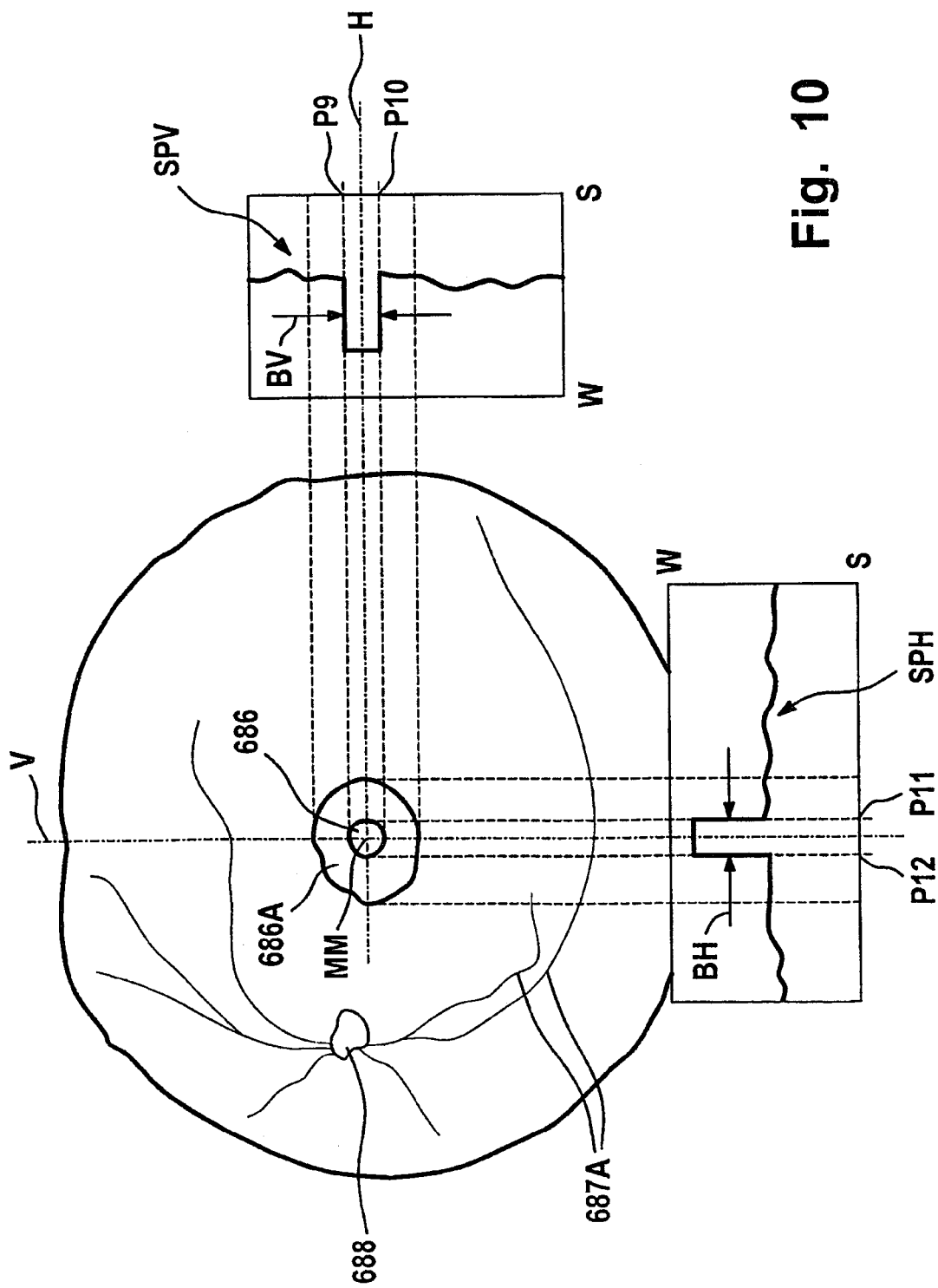
FIG. 10 is a view of a movement pattern for determining the macula center.

FIG. 10 is a view of the retina with the macula 686A, the fovea centralis 686 situated therein with the macula center MM, the blind spot 688 as well as several blood vessels 687A. The above-mentioned characteristics differ from one another and from the remainder of the retina by the brightness values of light beams reflected on them. Thus, for example, the fovea centralis 686 clearly reflects more than the remaining retina; the brightness values of light beams reflected on the fovea centralis are significantly closer to the brightness value W of a white reflection surface than those of light beams which are reflected in its environment and therefore have a brightness value situated closer to the brightness value S of a black reflection surface.

In an embodiment of the present invention, the retina is scanned along a horizontal line H and a vertical line V, which extend through a preliminary macula center obtained, for example, from the previously determined pupillary center in that, for example, the pupillary center itself is defined as a preliminary macula center, or the preliminary macula center is defined in a predetermined position with respect to the pupillary center, which may be determined, for example, empirically from preceding examinations of the relative positions of the pupillary and macula centers. Then, by means of the position of points P9, P10 or P11, P12, in which a significant jump occurs in the case of the vertical or horizontal scanning in the brightness course SPV or SPH, and/or by means of the distance BV or BH between these points analogous to the above-described methods for determining the pupillary center, the center of the fovea centralis 686 or of the macula center 686A are determined.

In addition, for example, the distance of points P9, P10, P11 or P12 from the detector can be determined, and the three-dimensional position of the macula center relative to the device according to the invention or the detector and/or relative to the pupillary center can thereby approximately be determined. From the three-dimensional position of the pupillary and macula center, for example, the three-dimensional position of the direction of vision, for example, relative to the detector, can then be determined.

4.2.4 Precision Determination of the Macula Center

Figure 11:
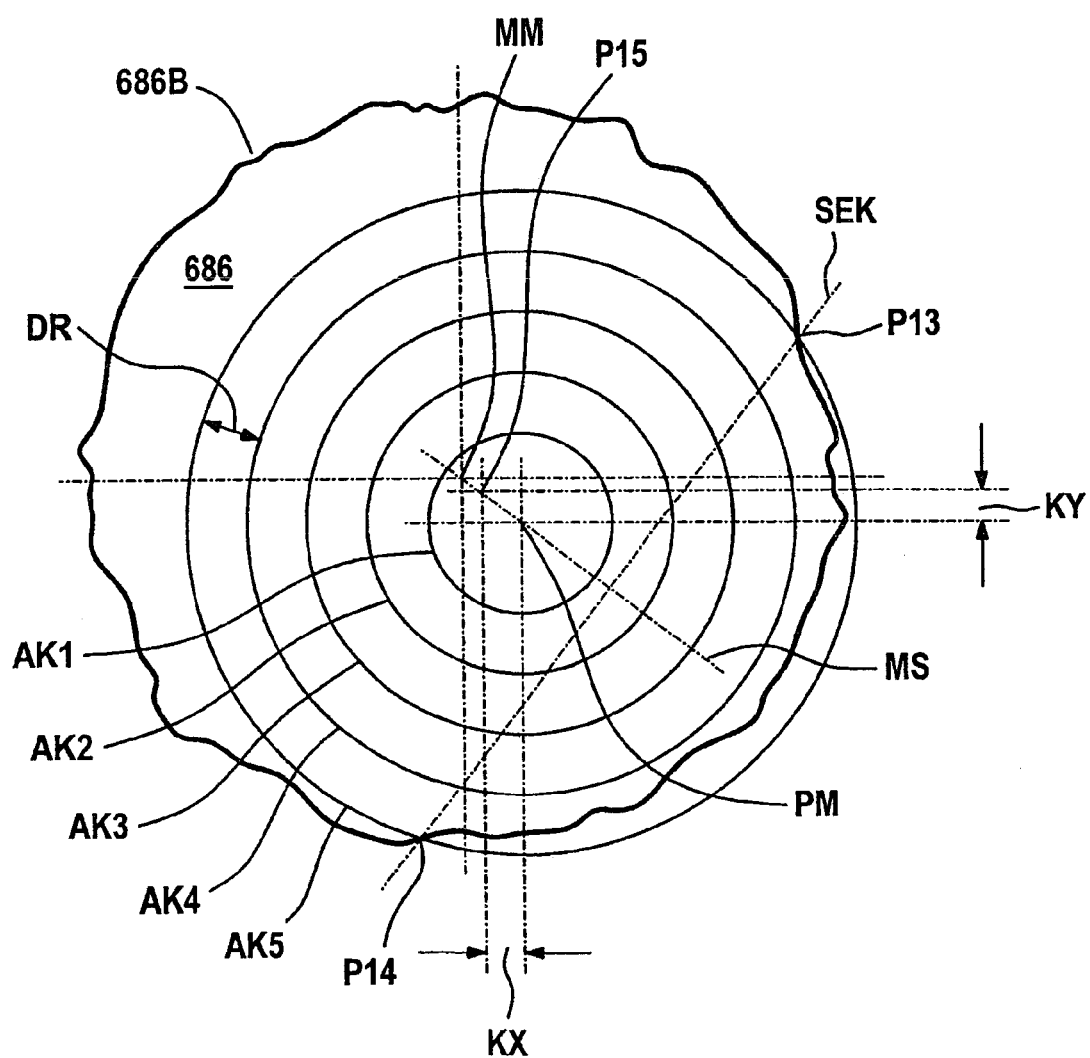
FIG. 11 also is a view of a movement pattern for determining the manular center.

By means of FIG. 11, a method for the precision determination of the macula center is described in detail analogously to the above-indicated method for the precision determination of the pupillary center. Beginning with the previously found pupillary center PM, which is used as the starting point, the retina is scanned in the region of the macula 686 in concentric circles AK1, AK2, . . . Akn, in which case the radius of a circle Aki is always larger than the radius of the preceding circle Ak(i−1). As soon as the brightness values detected along a circle (in FIG. 6A, circle AK5) in an area between a point P13 and a point P14 on the circumference of the circle have a clearly different value, the preliminary macula center PM will be displaced along the mid-perpendicular to the secant determined by P13, P14 into the new preliminary macula center P15. The process is repeated with a reduced difference between the radii of successive circles, starting with the circle that was still completely inside the macula, i.e., in the case of which the brightness values along the entire circumference of the circle approximately have a value characteristic of the macula and, for example, empirically determined and have no significant jumps. The process will be repeated until the difference between the radii of successive circles falls below a predefined threshold value or a circle extends approximately along the boundary of the macula, which is determined in that the brightness values along this circle have a plurality of signal jumps between the value characteristic of the macula and a value that is clearly above it. The macula center that was found last will be stored.

Concerning 4.2.5 Multi-Step and Analogous Methods

It was explained above how, by means of the reflected light beams, the pupillary and/or macula center can be roughly or precisely determined. Likewise, other significant characteristics of the eye, such as blood vessels of the retina, scars on the cornea or the lie, can also be determined. For this purpose, a scanned reflex image, for example, can be analyzed by means of an image or pattern identification and significant patterns (such as blood vessels, scars or the like) can be located.

Concerning 4.3.2 Determination of the Orientation of the Retina Reflex Image (Retina Map)

Figure 12:
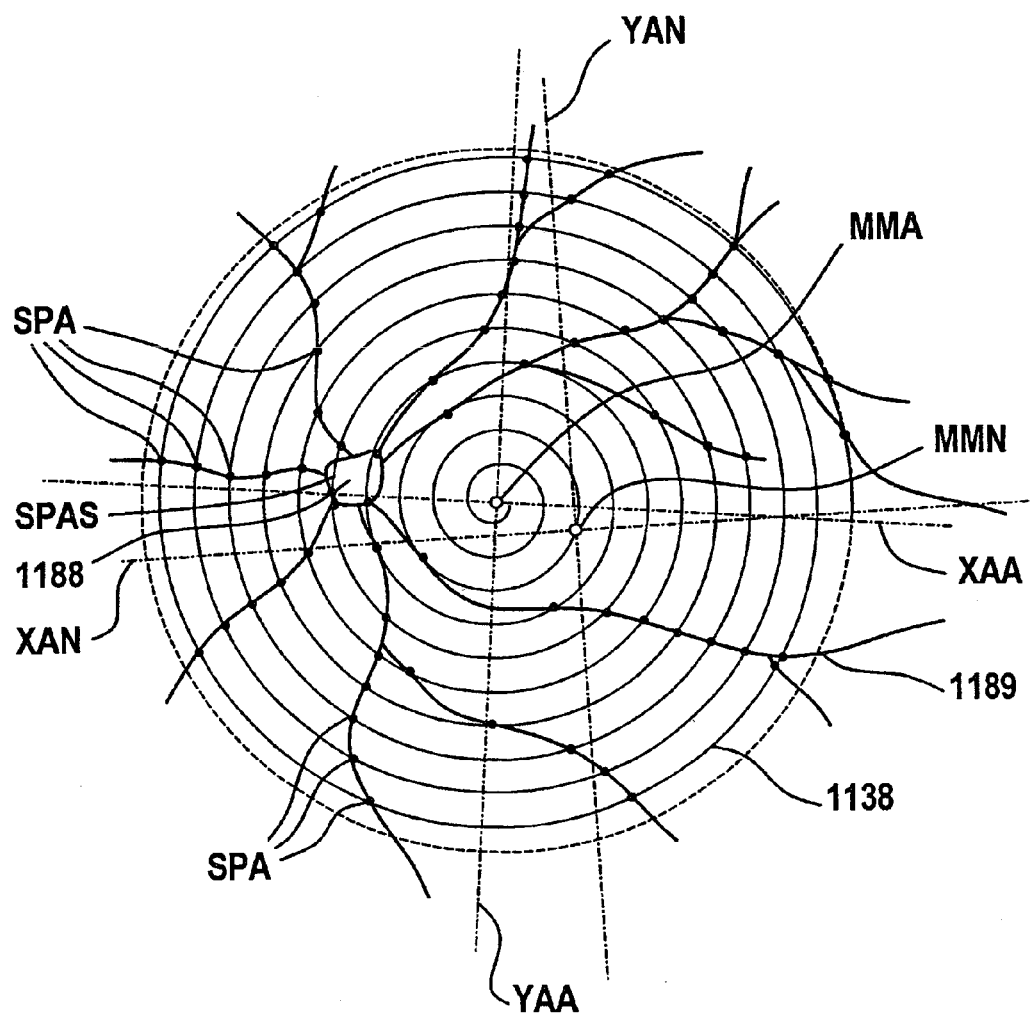
FIG. 12 is a schematic view of the retina with a spiral-shaped scanning pattern.

FIG. 12 shows a two-dimensional image of the retina of an eye having a blind spot 1188, the macula center MMN and diverse blood vessels. The retina is scanned by means of a suitable movement pattern, for example, as illustrated in FIG. 12 along a spiral 1138. In this case, as described above, the scanning pattern may be oriented according to the old macula center MMA as the reference point, which had been determined and stored in an earlier step. While spirals are used for the purpose of an explanation in the example, the scanning may also take place along concentric circles, along a rectangle grid or the like.

The macula center as a reference point may be determined by means of one of the above-described methods or by means of the present method, which had been carried out at an earlier point in time. Starting at the old macula center MMA, the detector of the device according to the invention detects the brightness values of the light beams which are reflected along the spiral. In this case, points SPA of the curve, which are situated on a blood vessel, have different brightness values than points on the remainder of the retina; the same applies to points SPAS which are situated on the blind spot 1188 or to points MMN which are situated on the macula. The thus obtained brightness values are stored as a retina map.

Figure 13:
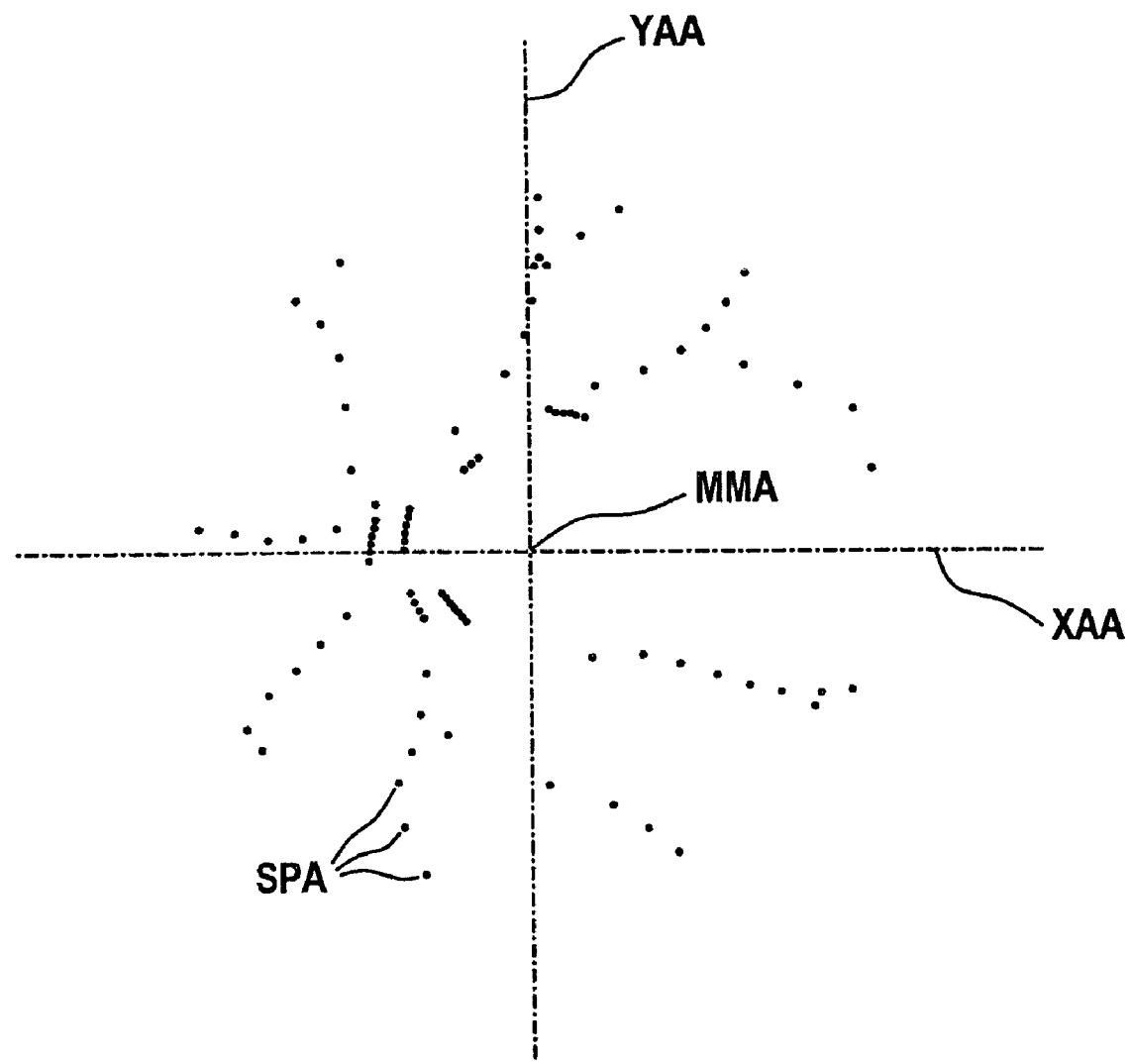
FIG. 13 is a view of a scanned image of the retina from FIG. 12.

FIG. 13 shows a thus determined retina map where the brightness values are stored, for example, in the binary form; i.e., each point whose brightness value exceeds a certain characteristic value is provided with a 1, otherwise, it is provided with a 0. A retina map can expediently be stored in the form of a matrix.

By comparing the thus determined new retina map with an old retina map determined at an earlier point in time, corresponding software can determine the displacement and rotation of the new retina map with respect to the old retina map and thereby determine the orientation change of the eye. For this purpose, preferably first by means of one of the above-described methods, the new, i.e., actual macula center MMN is determined whose position relative to the old macula center MMA results in the displacement of the new retina map with respect to the old one; i.e., the pertaining displacement vector W is the vector of MMA to MMN. Subsequently, two preferably orthogonal axes XAN and YAN respectively are determined in the new retina map, which intersect with one another in the new macula center MMN and are oriented by means of certain characteristic features of the scanned points of the retina. For example, the axis XAN may extend through points which, because of their arrangement or their brightness values, are recognized as part of the blind spot. Subsequently, the old retina map is displaced by the vector W, so that the old macula center MMA is situated on the new macula center MMN and is subsequently rotated about this point MMA=MMN such that the old axes XAA and YAA respectively will be situated on the new axes XAN and YAN respectively. The angle of rotation occurring in this case, together with the displacement vector W, describes the position and orientation change of the eye relative to the device with respect to the position when the old retina map was taken.

Figure 14:
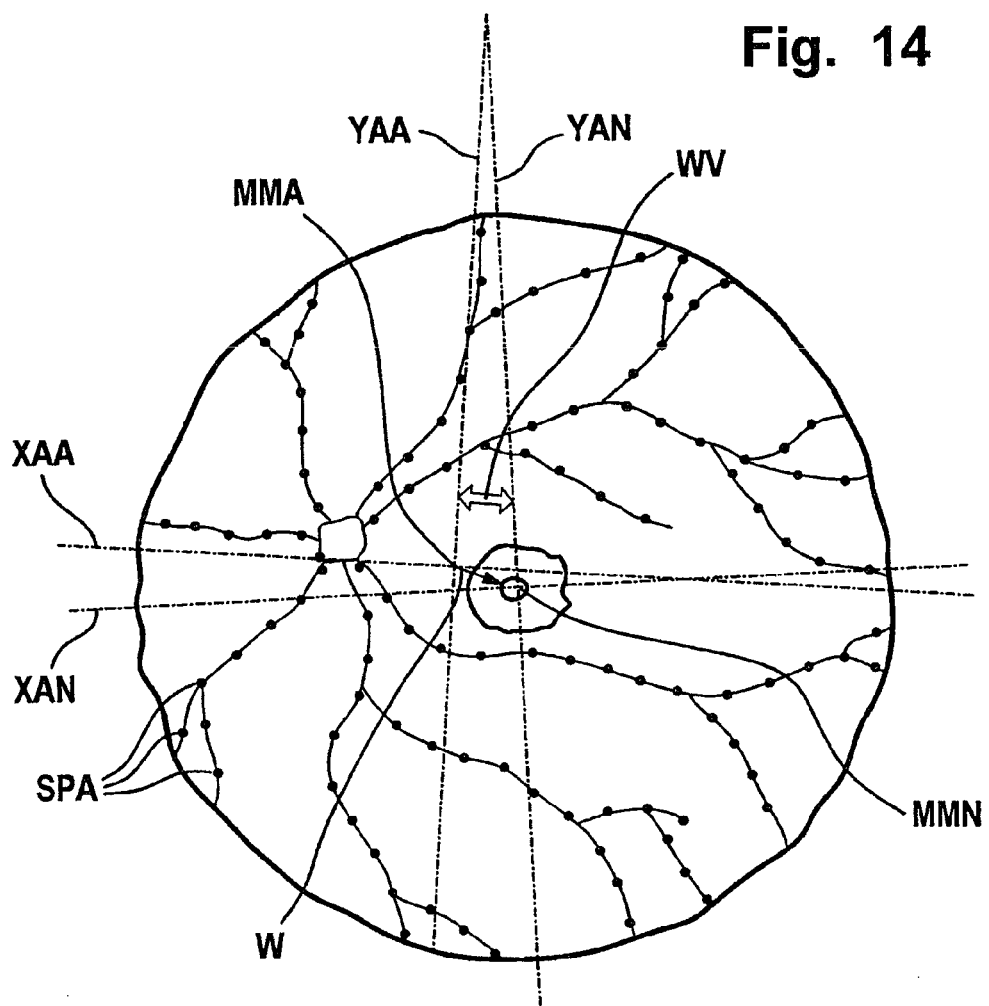
FIG. 14 is a schematic view of the retina with old and new axes.

Likewise, as illustrated in FIG. 14, a corresponding pattern identification and processing software can also directly make an actual, i.e., newly scanned retina reflex image or an actual retina map congruent with a stored old retina map or a retina reflex image. The rotation and/or displacement carried out in the process again describes the position and orientation change of the eye with respect to the position which corresponds to the old retina map or the retina reflex image. In this case, it is pointed out that an actual retina reflex image may advantageously be scanned or stored with clearly fewer scanning elements (points). As a rule, these will nevertheless be sufficient for making the actual image and the reference image congruent, in which case, advantageously fewer points have to be scanned or processed.

In addition, for example, the distance of a point on the retina from the detector can be detected, and approximately the three-dimensional position of the retina and therefore of the eye relative to the device according to the invention or to the detector can be determined.

Figure 15:
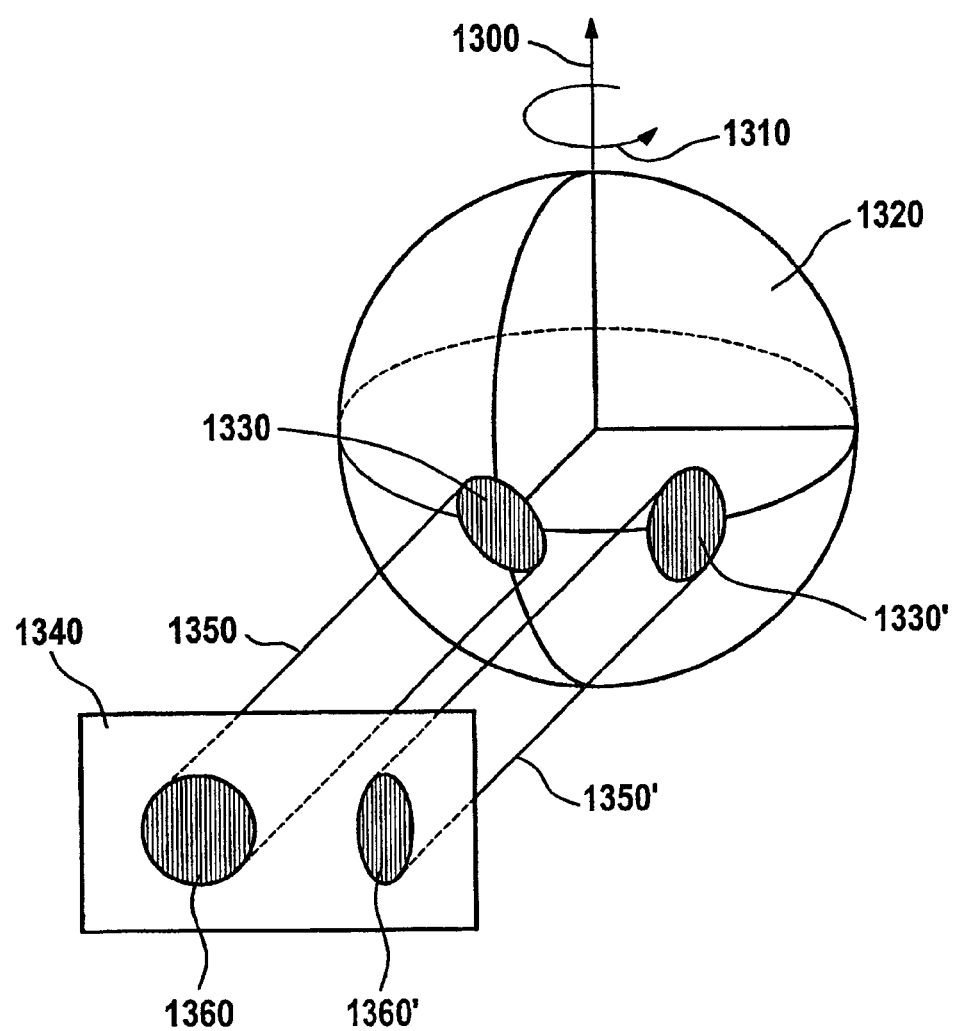
FIG. 15 is a schematic view of an eye with the pupil in a reference and rotated position a well as the corresponding scanned image.

Likewise, as illustrated above, the distortion of the reflex image, for example, of the reflex image of the macula or of the retina, can be used for determining the orientation of the eye, as illustrated in FIG. 15 by means of a very simplified model. FIG. 15 is a perspective view of an eye 1320 which is rotated by the angle 1310 about the axis 1300.

In the non-rotated condition, a device according to the invention determines an image 1360 of the pupil by means of light beams 1350 reflected on the iris. In the rotated condition, the light beams 1350' reflected on the iris in the detector 1340 supply the displaced and distorted image 1360' of the pupil 1330' of the rotated eye. From the displacement and distortion of the image 1360' in comparison with image 1360, the rotation 1310 of the eye 1320 can be determined correspondingly. In the knowledge of the actual physical shape, for example, the circularity of the pupil, the orientation relative to the detector can also be determined from the distorted image. The actual physical shape may have been determined, for example, empirically.

In addition, for example, the distance of a point on the iris to the detector can be determined, and approximately the three-dimensional position of the iris or of the pupil and thus of the eye relative to the device according to the invention or to the detector can thereby be determined.

Concerning 4.3.3 Orientation with Respect to the Environment and/or Device

In the following, different possibilities according to the invention for determining the orientation of the eye relative to the environment or the device are explained by means of FIGS. 16, 16A-16E. For the purpose of improved clarity, the representation and description is limited to the simplified plane case. The methods can analogously also be applied to the generally spatial case. In addition, the distance of one or more scanned points of the eye can be determined, for example, relative to the detector in that, for example, a frequency-modulated light signal is beamed onto this point and the reflected light beam is detected. From the frequency of the detected light beam, the point in time of its emission and thereby its propagation time can be determined, from which, in turn, a distance from the detector or from the projection system can be determined. The three-dimensional position of the eye relative to the device according to the invention can thereby also be determined.

FIG. 16 schematically shows an eye 200 in a reference position and in an orientation (indicated by a broken line and marked by ') rotated in comparison with the reference position by the angle α with respect to the environment, characterized in each case by the axis 210 and 210' of vision respectively which extends through the centers of the pupil 220 and 220' and of the macula 230 and 230' respectively. In addition, the blind spot 240 and 240' respectively is marked on the retina of the eye 200. The environment 250 is outlined here by an incremental black-and-white pattern. In an embodiment of the present invention, the environment 250 can be photographed by a camera (not shown) which is rigidly connected with the device according to the invention and, in a preferred embodiment, is arranged approximately confocally with respect to the eye 200.

In the reference position, a device according to the invention may, for example, scan the reflex image of the environment 250 (environment reflex image, passage scanning) illustrated in FIG. 16A. In addition or as an alternative, a device according to the invention may also actively scan a portion of the retina of the eye 200. FIG. 16B schematically shows the corresponding image with the macula 230A and the blind spot 240A (retina reflex image, active scanning). When the light beamed in for the active scanning is appropriately modulated, the environment reflex image and the retina reflex image can be created separately from one another. For example, for the active scanning, infrared light is additionally beamed in during a certain time period T1, while, in a subsequent time period T2, no light beams in actively. A subtraction of the image of the retina taken during the period T2 from the image of the retina taken during period T1 approximately supplies the retina reflex image, while image taken during period T2 represents the environment reflex image.

While the environment reflex image shows structures (edges, etc.) which are fixed relative to the environment (environment image), the structures in the retina reflex image are fixed relative to the eye (eye image).

By means if a suitable image identification software, both images in FIGS. 16A and 16B can be compared with one another and, for example, the distance A1 between a significant edge in the reflex image of the environment and the macula center can be determined. Analogously, also an image of the environment (environment image) taken by the camera and the image of the retina can be compared with one another and a distance can also be determined between a significant edge and the macula center.

Orientation of the Eve with Respect to the Environment

By means of the relative position of significant characteristics in the environment image 16A and the eye image 16B, outlined, for example, by the distance A1 between a significant edge and the macula center, an orientation of the eye with respect to the environment can be determined. For example, it may be determined that the direction of vision of the eye points to the right edge of the highest black bar in the environment.

Change of Orientation of the Eye with Respect to the Environment

When the orientation of the eye 200 changes with respect to the environment such that the visual axis 210 changes by the angle α into the new visual axis 210' and, in the process, the device remains constant relative to the environment, the scanning of the environment reflex image shows the image illustrated in FIG. 16C which, in the illustrated example, with the exception of the distortion because of the two-dimensional imaging of the three-dimensional structure, is identical with that of FIG. 16A. A scanning of the retina supplies the retina reflex image illustrated in FIG. 16D with the macula 230A and the blind spot 240A. A comparison of this image of the retina with the reflex image of the environment (FIG. 16C) or the picture of the environment (FIG. 16) taken by the camera again supplies a value A2 of the distance between a significant edge in the image of the environment and the macula center. From the change of this distance A1 to A2, the rotation a of the eye with respect to the environment can be determined.

Change of Orientation of the Device with Respect to the Environment

When the orientation of the eye does not change with respect to the device, but the orientation of the device does so with respect to the environment that the visual axis 210 is again rotated by the angle α into the axes of vision 201', a detection of the image of the environment reflected on the retina and/or of an image of the environment taken by the camera supplies the environment reflex image illustrated in FIG. 16E. From a comparison of significant edges, an image correlation or the like between this image and the first taken environment reflex image from FIG. 16A, a rotation of the device with respect to the environment can then be determined analogously.

A scanning of the retina, in turn, supplies the retina reflex image illustrated in FIG. 16B with the macula 230A and the blind spot 240A, from which it can be concluded that the position of the eye relative to the device has not changed.

As described above, the change of the orientation of the eye with respect to the environment is composed from the orientation change of the eye with respect to the device and the orientation change of the device with respect to the environment. Their determination was in each case illustrated individually. In the case of a simultaneous change of the orientation of the device and the eye, both effects are superimposed on one another and can be determined by a corresponding linking of both methods.

On the whole, different possibilities exist in the above-described example for determining the orientation of the eye, which will be listed in the following. In the case of a device according to the invention and a method according to the invention respectively, several of these possibilities can be combined in order to simultaneously determine several relative orientations or check results and, as required, correct them. As initially mentioned, the variants are explained by means of a simplified plane representation; in the general spatial case, corresponding methods should be used analogously. In addition, the three-dimensional position of the eye can be determined, for example, by means of a distance measurement between a part of the eye and the detector.

Camera Picture—Retina Image

When the picture of the environment taken by a camera fixedly connected with the device (FIG. 16) is compared with the image of the retina which is, for example, the result of an active scanning (FIG. 16B, 16D), significant characteristics in the environment image (edges, etc.) and in the retina image (macula, etc.) can be assigned to one another. By means of this relative position (for example, distance A1), an orientation of the eye relative to the environment can be determined. From the change of the relative position of these characteristics with respect to one another (distance A1, A2, etc.), the change of the orientation of the eye with respect to the environment can be determined. Likewise, the two images also can be made congruent (for example, by a correlation method or by rotation and displacement). From the resulting values (for example, correlation factors or angle of rotation and displacement), in turn, the orientation change of the eye with respect to the environment can be determined.

Camera Picture/Environment Reflex Image Structure

From the change of the picture of the environment which was taken by a camera fixedly connected with a device or which is reflected by the retina and detected by a device according to the invention, the change of the orientation of the device with respect to the environment can be determined. For this purpose, for example, two environment reflex images (FIG. 16C, 16E) are compared with one another which were taken at a time interval from one another. When, in the interim, the orientation of the device with respect to the environment has changed by the angle α, significant patterns (for example, continuous vertical bars) have a distance A3 from one another, from which the orientation change a is obtained. Likewise, the two images may also be made congruent (for example, by a correlation method or by rotation and displacement). From the resulting values (for example, correlation factors or angle of rotation and displacement), the orientation change of the eye with respect to the environment can be determined.

Orientation Eye—Device

According to the invention, a marker may be present on a spectacle lens in front of the eye or may be arranged in any other suitable form in a fixed position relative to the device in front of the eye.

For this purpose, FIG. 17A is a simplified schematic plane representation in the manner of an example of an eye 200 with the visual axis 210 and the macula 230. A spectacle lens 260, which has a marker 261 in the field of vision of the eye, is arranged in front of the eye. FIG. 17B shows an image of the environment, which is reflected by the retina and in which the marker 261 can be recognized (environment reflex image), and is superimposed on an image of the retina reflex with the macula 230.

By means of the relative position of the retina reflex image (eye image) with respect to the marker in the environment reflex image (device image), indicated by the distance A4 between the macula center and a significant edge of the marker, an orientation of the eye relative to the device can be determined. An image fixed with respect to the device, such as the image of the marker 261, can be used as the device image.

Likewise, just as a result of the relative position of the eye image, indicated, for example, by the macula center within the image of FIG. 17B, an orientation of the eye with respect to a device-fixed coordinate system, given, for example, by the left or lower image edge in FIG. 17B can be determined, without requiring a marker.

FIG. 17C also shows the eye 200, whose orientation, characterized by the visual axis 210, changes with respect to the spectacle lens 260 by the angle α. FIG. 17D, again in a superimposed manner, shows an image of the environment, which is reflected by the retina and has the marker 261, and an image of the retina with the macula 230. In this case, the image of the retina can be detected, for example, by means of an active scanning.

A comparison of the two images 17B and 17C indicates that the spacing A4 of the images of the marker 261 and of the macula 230 changes corresponding to the orientation change a of the eye relative to the device. From the change of this spacing, the change of the orientation can therefore be determined. As mentioned above, instead of the marking 261, for example, the geometrical shape of the spectacle edge itself can also be chosen as the reference.

Likewise, also without a marker, the orientation change of the eye relative to the device can be determined just from the change of the relative position of the macula (eye image) within the device-fixed coordinate system (again given by the left or lower edge in FIG. 17D).

Different possibilities according to the invention were explained above as to how, by means of light beams, which are reflected by a part of an eye, characteristic features of the eye can be determined and as to how they can be used for determining the orientation of the eye relative to the environment and/or relative to the device.

After several embodiments of the different features of a device according to the invention and of a method according to the invention were described in detail above, which, in an embodiment of the present invention, can appropriately be combined with one another, in the following, several embodiments of the present invention will be described in detail as examples.

As initially illustrated, the knowledge of the momentary orientation of an eye offers a plurality of possibilities:

5.1 Medicine

In the field of medicine, a device for treating the eye by a device which receives the momentary orientation or change of orientation of an eye from a device according to the invention and appropriately processes these signals (for example, within a position control during which orientation changes are used as a deviation), can compensate voluntary and mainly involuntary eye movements (for example, so-called saccade movements or microtremors), so that, for example, a laser beam for the treatment of the eye or a light signal for examining the eye (is applied?) in a stationary manner or is guided on a fixed trajectory relative to the eye.

5.2 Psychology, Neurology

In the fields of neurology or psychology, certain eye movements, i.e., orientation changes, can be used as diagnostic aids, for example, for the prediction of an epileptic seizure, of a blackout, for diagnosing schizophrenia, or the like.

Significantly more extensive applications are opening up if, in particular, the direction of vision of the eye is determined: In psychology, for example, identification patterns when viewing certain images can be detected and analyzed.

5.3 Direction of Vision

The knowledge of the direction of vision makes it possible to determine in which direction the user is looking. This can be used for identifying a (possibly only virtual) object on which the user is focusing. For this purpose, for example, an environment reflex image of the retina can be scanned. When, for example, by means of an active scanning, the position of the pupillary center or of the macula center is determined within this environment reflex image, this point can be determined as the point at which the user is just looking. An image identification can, for example, identify the object therefrom at which the user is just looking.

In this case, the user can indicate, for example, by blinking, key pressure or the like, that he is focusing on the selected object.

Likewise, it can also be determined after a certain time period in which no eye movements or only slight eye movements have occurred that the user is focusing on an object and this object can be determined from the determined direction of vision.

Likewise, the user can also be instructed to focus on a certain point or object (which under certain circumstances may also be moved relative to the user). While the user is focusing, an orientation of his eye may be carried out simultaneously. For example, the position of the pupillary center can be determined in each case. From the correlation of the focused object and the respectively determined orientation, a correlation can then, for example, be determined between the orientation of the eye and a visual axis, which may, for example, be determined by the straight connecting line from the focused point to the pupillary or macula center. By means of this correlation, the orientation of the visual axis relative to the device can be determined from a determined orientation of the eye (for example, the position of the pupillary center).

5.4 Focus of the User

A suitable device, which receives the signal as to on which image cutout the user is just focusing and possibly identifies this image cutout by means of image identification, can process this information and trigger a desired action:

A launcher can select a desired target in this manner whose coordinates are used, for example, as target data of a rocket missile;

a user (for example, in the household or in a production operation) can select a device (such as a light switch, an appliance or a machine tool) that is to be activated, deactivated or controlled in another manner. A control device receives the signal as to where the viewer is looking; identifies the device or the switch at which he is looking, and controls the selected device corresponding to a predetermined control program. The user, for example, looks at the system switch of the television; blinks several times (in order to exclude involuntary blinking) and the device switches on the television. Then the viewer looks at a certain program field, and the device switches the television to the assigned program, which again was indicated by repeated blinking, etc.

The patterns on which the user is to focus do not necessarily really have to exist, they may be present only virtually. For example, a computer screen displays different fields which each correspond to a menu item to be selected, or such fields are projected directly on the user's retina by the device.

5.5 Projection

For the projection of information onto the retina of the eye, as disclosed, for example, in PCT Applications PCT/EP00/09843, PCT/EP00/09840, PCT/EP00/09841, PCT/EP00/09842 and PCT/EP01/05886 by the applicant, it is necessary or advantageous to correlate the (image) information merged into the eye with direction of vision of the eye:

When the information is projected in additionally to the environment image which the user perceives, for example, by means of semitransparently metal-coated spectacles (see the "Optical Device Section"), it may be advantageous to correlate the information with the environment image perceived by the retina in such a manner that the merged-in information appears stationary relative to the environment. For example, for this purpose, the image of the environment reflected by the retina can be detected in the detector, can be appropriately processed and, while utilizing the determined orientation of the eye, can be congruently with the actually perceived environment image projected back into the eye.

In addition, for example, by means of a camera, a picture can be taken of the environment, can be processed in an appropriate manner and, while utilizing the determined orientation of the eye, can be projected into the eye such that it appears congruent with the actually perceived image. As a result, it becomes possible to take an infrared image of the environment, for example, by means of a camera and to merge the resulting environment image as additional information into the eye in order to improve the vision in fog, at night or under other difficult visual conditions.

Likewise, the camera may have a binocular lens system for enlarging remote images. Then, for example, in the center of the environment image perceived by the eye, an enlarged image detail can be projected into the eye which, compared to conventional binoculars, may have the advantage that the marginal areas of the environment image are not enlarged and therefore the orientation of the user with respect to the environment is not impaired or not as significantly impaired. As an alternative, a complete enlarged image of the environment can also be projected into the eye which covers the naturally perceived environment image, in which case small relative movements of the device, which result, for example, from the natural muscular tremors or shocks during the car drive, are compensated such that the "binocular" image appears stationary to the user. Such a binocular device avoids the micro movements in the case of conventional binoculars which are perceived to be disturbing.

Likewise, it becomes possible by means of determining the orientation of the eye to project information into the eye such that it moves relative to the environment or appears to be stationary relative to a moving object. For example, the distance to a vehicle driving ahead could be measured and projected into the driver's eye in such a manner that the information seems fixed relative to the vehicle driving ahead. The driver thereby receives necessary information without having to look away from the vehicle driving ahead. Inversely, for example, a text to be read can be projected into the eye such that it seems to move in front of the viewer's focus (i.e., the area of the perceived image at which the interest is aimed) corresponding to a predetermined movement pattern (for example, uniformly from the right to the left, discretely as groups of words or letters, etc.). Likewise, a text to be read can be projected into the eye such that it seems to be stationary with respect to the environment in that, for example, the determined orientation changes are taken into account during the projection of the text.

When, in contrast, the information is projected into the eye without any simultaneous natural perception of the environment, as it occurs, for example, in the case of virtual-reality glasses where the user perceives only the images projected into the eye, the determination of the direction of vision of the eye makes it possible to adapt the projected-in information, for example, the view of a virtual landscape, to the user's direction of vision. Thus, when the viewer looks to the left by rotating his eye relative to the glasses, a device according to the invention will recognize this orientation change and will correspondingly change the apparent angle of view with respect to the virtual landscape.

In the following, the essential points are summarized again by means of groups of characteristics which, each separately and in combination with one another, characterize the present invention in a special manner.

1. Device according to the invention or a method according to the invention for determining the position and/or the orientation, particularly the direction of vision, of an eye, a starting point or an end point of a light beam reflected by a part of the eye and detected by a detector system and/or of a light beam projected by a projection system onto or into the eye quasi two-dimensionally describes a movement pattern of a scanning and/or projection movement in the eye when the direction of the light beam is changed with respect to the time according to the scanning or projection movement.

2. Device according to Point 1, having
 a shifting device which causes a reference point of the movement pattern to follow into the pupillary or macula center, and
 a determination device which uses the movement pattern of the scanning movement or projection movement for determining the pupillary center or the macula center.

3. Device according to Point 1 or 2, wherein the determination of the direction of vision of the eye takes place without being perceived.

4. Device according to one of the preceding claims, wherein the device is constructed to be wearable (portable), particularly in the form of spectacles.

5. Device according to one of the preceding points, wherein the projection system is projected (projects?) an infrared light beam onto the eye whose diameter is very small in comparison to the pupillary diameter, and the ocular, particularly the retinal reflex of the beam is detected.

6. Device according to Point 5, wherein the infrared light beam has a diameter of less than 100 μm at the air-cornea transition.

7. Device according to one of Points 5 to 6, wherein the infrared light beam has a diameter of less than 50 μm at the air-cornea transition;

8. Device according to one of Points 5 to 7, wherein the infrared light beam has a diameter of less than 10 μm at the air-cornea transition.

9. Device according to one of Claims 5 to 8, wherein the infrared light beam has a diameter of less than 5 µm at the air-cornea transition.

10. Device according to one of Claims 5 to 9, having a splitter mirror arranged in the infrared light beam, which splitter mirror allows only a small fraction of the infrared light beam to pass and reflects a correspondingly large fraction of the incident ocular reflex in the direction of a detector device.

11. Device according to one of the preceding points, wherein the projection system projects light in a pixel-type manner with a predefined pixel frequency onto the eye.

12. Device according to Point 11, wherein the projection system modulates the projected light with a frequency that is higher than the pixel frequency.

13. Device according to Point 11 or 12, wherein the projection system modulates the projected light with a frequency that is a multiple of the pixel frequency.

14. Device according to Point 13 which carries out the modulation such that detected projected light reflected back from the eye can be differentiated from the ambient light.

15. Device according to one of the preceding claims, wherein no active illumination of the eye takes place, and the detector system carries out a pixel-type scanning of the ambient light reflected back from the eye and/or of the light emitted by the eye.

16. Device according to one of the preceding points which illuminates the eye in a surface-type manner by infrared light, and wherein the detector system carries out a pixel-type scanning of the infrared light reflected back from the eye.

17. Device according to Claim 15 or 16, wherein the detector system is designed for scanning pixels of a size of less than 100 µm2 of the retina.

18. Device according to one of Points 15 to 17, wherein the detector system is designed for scanning pixels of a size of less than 25 µm of the retina.

19. Device according to one of the preceding points, having a surface that can be positioned in front of the eye, which has marker areas which reflect an incident projection beam originating from the projection system completely back in the direction of the detector system, as well as normal areas which guide an incident projection beam originating from the projection system in the direction of the center of the eye.

20. Device according to one of the preceding points which determines the position and/or orientation of the eye with respect to its environment in that the detector system detects the retinal structure of the eye as well as the environment reflex image superimposed thereon, determines the position of the fovea by means of the retina structure and identifies the area of the environment sighted by the fovea by means of a pattern identification.

21. Device according to one of the preceding points, which determines the direction of vision of the eye in that it determines the change of the relative position between the optical detector and/or projection system and the eye.

22. Device according to one of the preceding points, having a guiding device, which uses the information content of the light detected during the scanning movement for determining time-related changes of the relative position of the optical detector and/or projection system with respect to the optical system of the eye in order to cause the movement pattern of the scanning and/or projection movement to follow on the basis of the determined change of the relative position of the time-related position changes of the eye.

23. Device according to one of the preceding points, wherein the optical detector and/or projection system is a system for the emission of signals as a function of image information incident on the human retina.

24. Device according to one of the preceding points, having an analysis device, by which the information content, preferably as gray values, of the light reflected by the eye and detected by the detector system can be analyzed in two coordinates.

25. Device according to one of the preceding points, through which the movement pattern of the scanning movement passes several times, at least in sections, particularly repeatedly, until unambiguous values for the coordination of the pupillary or macula center are present.

26. Device according to one of the preceding points, which switches a starting pattern in front of the movement pattern of the scanning movement for determining the pupillary or macula center, which starting pattern, as a result of the analysis of the information content, preferably of the gray values, of the light detected by the detector system in two coordinates, is used for the rough determination of the coordinates of the pupillary center.

27. Device according to Point 27, having a reference point from which the starting pattern originates.

28. Device according to Point 26 or 27 which uses the coordinates determined during the rough determination of he pupillary center when defining the movement pattern of a subsequent scanning movement for the precision determination of the pupillary or macula center.

29. Device according to one of Points 27 to 29, wherein the starting pattern for the rough determination of the pupillary center comprises at least three linear movement sections, the first movement section preferably originating from the reference point, which intersects twice with a transition between the iris and the sclera of the eye, being followed by a second movement section, which extends along the mid-perpendicular of a first secant that corresponds to the first movement section between the two iris/sclera transitions, and the third movement section, in turn, standing perpendicularly on the second movement section and extending either through the center of the pupil determined during the second movement section by way of the information content, preferably by way of the gray values, of the detected light, or, in the center, intersecting a second secant formed by the second movement section with respect to two iris/sclera transitions.

30. Device according to one of the preceding points which, for the precision determination of the pupillary center, carries out a scanning movement in the pattern of a circular spiral or elliptic spiral or of concentric circles or ellipses around roughly determining coordinates of the pupillary center.

31. Device according to Point 31, wherein previously stored coordinates of the pupillary center are used as roughly determining coordinates of the pupillary center.

32. Device according to Point 31, wherein, roughly determined instantaneous coordinates of the pupillary center are used as roughly determining coordinates of the pupillary center.

33. Device according to one of Points 31 to 33 which recursively refines the roughly determining coordinates of the pupillary center by means of the information content, preferably by means of the gray values, of the light detected during the scanning movement for the precise determination of the pupillary center.

34. Device according to one of Points 31 to 34 which terminates the scanning movement for the precision determination of the pupillary center when the values, particularly the gray values, of the light detected during a cohesive scanning movement section passing through at least 360°, do not fall outside a predetermined area.

35. Device according to Point 30 which uses the point at which the third movement section crosses an iris/pupil transition for the second time as the starting point for a scanning movement for the precision determination of the pupillary or macula center.

36. Device according to one of the preceding points which, for the precision determination of the macula center and/or structure, carries out and/or repeats a radially increasing scanning movement originating from the coordinates obtained during the determination of the pupillary center in the pattern of a circular or elliptic spiral or of concentric circles or ellipses until the information content, preferably the gray values, of the light detected during the radially increasing scanning movement supplies a clear indication of the diameter and/or the center of the macula.

37. Device according Point 31 which terminates the scanning movement for the precision determination of the macula center and/or structure when the information content, preferably the gray values, of the light detected during a cohesive scanning movement section passing through at least 360° repeatedly has a clear signal jump from a light value to a dark value and vice-versa.

38. Device according to one of the preceding points which determines the relative position of at least one characteristic area of the retina with respect to the optical detector and/or projection system, and which uses the deviations of determined position data of this characteristic area from previously stored position data of this characteristic area for the determination of the spatial position and/or orientation of the eye with respect to the optical detector and/or projection system.

39. Device according to one of the preceding points which detects a representation of at least selected areas of the retina and stores it in an intermediate memory and, for determining a change of the spatial position of the eye, makes a comparison of the filed representation with information which the device has obtained from light scanned from the retina and detected during an actual scanning movement.

40. Device according to one of Points 38 to 40 which uses the iris, the sclera, the cornea and/or another structure of the eye instead of the retina or together with the retina.

41. Device according to Point 39 which, as a characteristic area, uses at least one section of the vessel structure of the retina.

42. Device according to one of the preceding points, wherein light is detected in the visible and/or in the infrared range by the detector system.

43. Device according to one of the preceding points, having a memory device in which the coordinates of the pupillary or macula center with respect to a reference point on the optical detector and/or projection system can be stored.

44. Device according to one of the preceding points, having a light-guiding arrangement by means of which the beam path of the light detected by the detector system and/or projected by the projection system can be controlled corresponding to the movement pattern of the scanning or projection movement, and an adjusting device by means of which a neutral center position of the beam-guiding arrangement can be caused to follow while using the change of the coordinates of the pupillary or macula center.

45. Device according to one of the preceding points, having a beam-guiding arrangement which can control the beam path of the light detected by the detector system in such a manner that it describes a circular or elliptic spiral or concentric circles or ellipses in the eye.

46. Device according to Point 46, wherein the position of the beam-guiding device is used for determining the relative position of at least one characteristic area of the retina with respect to the optical detector and/or projection system.

47. Device according to one of the preceding points, with a surface having a predefined geometrical shape which can be positioned in front of the eye and by way of which light can be projected from the projection system into the eye, the geometrical shape of the surface being used for determining the relative position of at least one characteristic area of the retina with respect to the optical detector and/or projection system.

48. Device according to one of the preceding points, having a memory device by means of which the rough coordinates of the pupillary center can be stored corresponding to a rough determination of their position.

49. Device according to one of the preceding points, having
   a device for determining the relative position of at least one characteristic area of the retina with respect to the optical detector and/or projection system,
   a comparator device by means of which the deviations of determined position data of this characteristic area from previously stored position data of this characteristic area can be used for determining the spatial position of the eye with respect to the optical detector and/or projection system.

50. Device according to one of the preceding points, having a readjusting device by means of which the movement pattern of the scanning and/or projection movement can be readjusted corresponding to deviations of determined position data of at least one characteristic area of the retina from previously stored position data of this characteristic area, in order to shift the center of the movement pattern of the scanning and/or projection movement, which was previously situated in the pupillary or macula center, again into the pupillary or macula center of the eye, and/or in order to cause the movement pattern to follow the time-related position changes of the optical system of the eye.

What is claimed is:

1. A device for determining the position and/or the orientation of an eye, comprising:
   a detector system for detecting light reflected by at least a part of the eye, wherein the position of the pupillary center of the eye is determined from the detected light and is used for determining the position and/or orientation of the eye relative to the device,
   a camera for capturing a first camera image and at least a second camera image by photographing the environment at a time interval from one another, wherein said camera is rigidly connected with the device,
   wherein the first camera image and the at least second camera image are compared with one another in a common coordinate system for determining the position and/or orientation of the device relative to the environment; and
   a projection system for projecting perceivable information into the eye such that it is correlated with the determined position and/or orientation of the eye and the determined position and/or orientation of the device,
   wherein the device is integrated into a portable object which is movable relative to the environment and relative to a carrier of the device.

2. The device according to claim 1, wherein the comparison of the first camera image and the at least second camera image comprises identifying at least one significant pattern of the environment in the first camera image and in the at least second camera image, and determining the orientation of the device with respect to the environment from the change of position of at least one significant pattern of the environment in the common coordinate system.

3. The device according to claim 1, wherein the projection system projects such that the projected perceivable information appears stationary relative to the environment.

4. The device according to claim 1, further comprising a means for determining the distance of the pupillary center of the eye from the detector and determining the three-dimensional position of the eye from the determined position of the pupillary center of the eye and the determined distance from the detector.

5. The device according to claim 1, further comprising an orientation determining device comprising a GPS receiver and the pertaining analysis device for determining the position of the device from received GPS signals, wherein the orientation determining device is fixedly connected to the device.

6. A device for determining the position and/or orientation of an eye, comprising:
 a detector system for detecting at least one environment reflex image by detecting ambient light which is incident on and at least partially reflected by a part of the eye,
 a camera for capturing at least one environment image by photographing the perceived environment,
 wherein said camera is rigidly connected with the device,
 a determination device which identifies a significant structure in both the environmental reflex image and the environment image and determines the orientation of the eye relative to the environment from the spatial assignment of the positions of said significant structure in the environmental reflex image and the environment image;
 a projection system for projecting perceivable information into the eye such that it is correlated with the determined position and/or orientation of the eye,
 wherein the device is integrated into a portable object which is movable relative to the environment and relative to a carrier of the device.

7. The device according to claim 6, wherein the determination device identifies a significant structure in both the environmental reflex image and the environment image by means of pattern identification.

8. The device according to claim 6, wherein said camera is arranged approximately confocal with respect to the eye.

9. The device according to claim 6, wherein the deviations of the determined position data of said significant structure from previously stored position data of this significant structure are used for the determination of the spatial position and/or orientation of the eye.

10. The device according to claim 6, with a projection device which projects perceivable information into the eye such that it is correlated with the determined orientation of the eye.

11. The device according to claim 6, comprising an orientation determining device, particularly at least one from laser triangulation, radar, GPS receiver, for determining the orientation of the device relative to the environment.

12. A device for determining the position and/or the orientation of an eye, comprising:
 a detector system for detecting light reflected by a part of the eye,
 wherein the position of the pupillary center of the eye is determined from the detected light and is used for determining the position and/or orientation of the eye relative to the device,
 an orientation determining device comprising a GPS receiver and a pertaining analysis device for determining the position of the device from received GPS signals, wherein the orientation determining device is fixedly connected to the device; and
 a projection system for projecting perceivable information into the eye such that it is correlated with the determined position and/or orientation of the eye and the determined position and/or orientation of the device,
 wherein the device is integrated into a portable object which is movable relative to the environment and relative to a carrier of the device.

13. The device according to claim 12, wherein the projection system projects such that the projected perceivable information appears stationary relative to the environment.

14. The device according to claim 12, further comprising a means for determining the distance of the pupillary center of the eye from the detector and determining the three-dimensional position of the eye from the determined position of the pupillary center of the eye and the determined distance from the detector.

15. The device according to claim 12, further comprising a camera for capturing a first camera picture and at least a second camera picture by photographing the environment at a time interval from one another,
 wherein said camera is rigidly connected with the device, and
 wherein the first camera image and the at least second camera image are compared with one another in a common coordinate system for determining the change of position and/or orientation of the device relative to the environment.

* * * * *